US010960097B2

(12) United States Patent
McGlade et al.

(10) Patent No.: US 10,960,097 B2
(45) Date of Patent: Mar. 30, 2021

(54) COMPOSITE MEMBRANE

(71) Applicant: S. C. Johnson & Son, Inc., Racine, WI (US)

(72) Inventors: Michael J. McGlade, Loveland, CO (US); Nitin Sharma, Kenosha, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 48 days.

(21) Appl. No.: 15/559,355

(22) PCT Filed: Mar. 17, 2016

(86) PCT No.: PCT/US2016/022770
§ 371 (c)(1),
(2) Date: Sep. 18, 2017

(87) PCT Pub. No.: WO2016/149451
PCT Pub. Date: Sep. 22, 2016

(65) Prior Publication Data
US 2018/0104372 A1    Apr. 19, 2018

Related U.S. Application Data

(60) Provisional application No. 62/165,039, filed on May 21, 2015, provisional application No. 62/135,359, filed on Mar. 19, 2015.

(51) Int. Cl.
*A61L 9/12*    (2006.01)
*A61L 9/02*    (2006.01)
*A61L 9/04*    (2006.01)

(52) U.S. Cl.
CPC .............. *A61L 9/122* (2013.01); *A61L 9/02* (2013.01); *A61L 9/044* (2013.01); *A61L 9/12* (2013.01);
(Continued)

(58) Field of Classification Search
CPC . A61L 9/122; A61L 9/02; A61L 9/044; A61L 9/12; A61L 2209/131;
(Continued)

(56) References Cited

U.S. PATENT DOCUMENTS 2,626,833 A * 1/1953 Valentine ............... B65D 75/26
239/56
4,161,283 A * 7/1979 Hyman ............... A01M 1/2044
239/55
(Continued)

FOREIGN PATENT DOCUMENTS

EP    0596212 A2    5/1994
GB    2161383 A    1/1986
(Continued)

OTHER PUBLICATIONS

"International Search Report" and "Written Opinion" for International Application No. PCT/US2016/022770, dated Sep. 5, 2016, 17 pages.
(Continued)

*Primary Examiner* — Joseph A Greenlund
(74) *Attorney, Agent, or Firm* — Quarles & Brady LLP

(57) ABSTRACT

A refill cartridge for a volatile composition includes a reservoir, a volatile composition within the reservoir, and a composite membrane in fluid communication with the reservoir. The composite membrane includes a barrier layer having a thickness of less than about 10 μm and at least one support layer in contact with the barrier layer, the support layer having a thickness of at least about 10 um. The volatile composition is transported from the reservoir across the composite membrane at a flux of between 1 and 100 g/(m2-hr) at about 25° C. and about 101 kPa.

14 Claims, 6 Drawing Sheets

(52) U.S. Cl.
CPC ... *A61L 2209/131* (2013.01); *A61L 2209/133* (2013.01)

(58) Field of Classification Search
CPC .......... A61L 2209/133; A01M 1/2055; A01M 1/2044; A01M 29/12; A01M 9/122; A01M 9/02; A01M 9/044; A01M 2209/131; A01M 2209/133; B01D 69/12
USPC ................................................ 239/34, 53–56
See application file for complete search history.

(56) References Cited

U.S. PATENT DOCUMENTS

| | | | | |
|---|---|---|---|---|
| 4,285,468 | A * | 8/1981 | Hyman | A01M 1/2044 239/55 |
| 4,288,395 | A * | 9/1981 | Ewing | C04B 38/007 261/122.1 |
| 4,483,771 | A * | 11/1984 | Koch | A61L 9/00 210/490 |
| 4,614,299 | A * | 9/1986 | Van Loveren | A01M 1/2055 239/56 |
| 4,673,601 | A * | 6/1987 | Lambing | B65D 75/52 220/266 |
| 4,715,536 | A * | 12/1987 | Capizzi | A61L 9/12 239/54 |
| 4,753,389 | A * | 6/1988 | Davis | A61L 9/01 239/56 |
| 4,804,142 | A * | 2/1989 | Riley | A01M 29/12 239/56 |
| 4,955,945 | A * | 9/1990 | Weick | A61M 15/0011 128/203.12 |
| 5,071,704 | A * | 12/1991 | Fischel-Ghodsian | A01N 25/18 428/354 |
| 5,372,303 | A * | 12/1994 | Paul | A61L 9/037 239/56 |
| 5,395,047 | A * | 3/1995 | Pendergrass, Jr. | A61L 9/12 239/34 |
| 5,455,043 | A * | 10/1995 | Fischel-Ghodsian | A01M 1/2055 424/448 |
| 5,782,409 | A * | 7/1998 | Paul | A61L 9/12 239/56 |
| 6,109,537 | A * | 8/2000 | Heath | A61L 9/12 239/51.5 |
| 6,670,023 | B2 * | 12/2003 | Mueller | B32B 7/06 206/459.5 |
| 6,909,840 | B2 * | 6/2005 | Harwig | A01M 1/2072 392/395 |
| 7,422,782 | B2 * | 9/2008 | Haedt | B32B 7/06 428/213 |
| 7,441,360 | B2 * | 10/2008 | Christianson | A47G 1/0616 362/276 |
| 7,607,250 | B2 * | 10/2009 | Leonard | A61L 9/12 40/725 |
| 8,617,395 | B2 * | 12/2013 | Offeman | B01D 71/70 210/640 |
| 8,617,677 | B2 * | 12/2013 | Trouilhet | B32B 27/36 428/35.7 |
| 8,679,218 | B2 * | 3/2014 | Wertz | B01D 39/163 55/486 |
| 8,931,711 | B2 * | 1/2015 | Gruenbacher | A01M 1/2044 239/34 |
| 9,204,741 | B2 * | 12/2015 | Kunesh | A47G 1/141 |
| 9,205,163 | B2 * | 12/2015 | Westphal | A61L 9/12 |
| 9,248,210 | B2 * | 2/2016 | Kunesh | A61L 9/12 |
| 9,327,044 | B2 * | 5/2016 | Olchovy | A01M 1/2055 |
| 9,555,376 | B2 * | 1/2017 | Matviychuk | B22F 7/002 |
| 9,757,490 | B2 * | 9/2017 | Santini | B32B 15/20 |
| 10,143,766 | B2 * | 12/2018 | Gruenbacher | A61L 9/12 |
| 2001/0000235 | A1 * | 4/2001 | Bowen | B32B 27/322 428/500 |
| 2003/0068295 | A1 * | 4/2003 | Rohde | A61L 9/01 424/76.1 |
| 2003/0168521 | A1 * | 9/2003 | Skalitzky | A61L 9/03 239/57 |
| 2003/0183080 | A1 * | 10/2003 | Mundschau | C04B 35/117 95/55 |
| 2005/0145711 | A1 * | 7/2005 | Blondeau | A61L 9/12 239/60 |
| 2005/0244307 | A1 * | 11/2005 | Gygax | A61L 9/035 422/124 |
| 2007/0131609 | A1 * | 6/2007 | Ramaswamy | C04B 38/00 210/490 |
| 2007/0160809 | A1 * | 7/2007 | Juran | A61L 9/042 428/138 |
| 2009/0238787 | A1 * | 9/2009 | Finke | A61K 8/34 424/65 |
| 2010/0022993 | A1 * | 1/2010 | Gordon | A01M 1/2044 604/892.1 |
| 2010/0264232 | A1 * | 10/2010 | Gruenbacher | A61L 9/04 239/6 |
| 2010/0270392 | A1 * | 10/2010 | Trent | A01M 1/2077 239/55 |
| 2010/0308130 | A1 * | 12/2010 | Gruenbacher | A01M 1/2033 239/34 |
| 2011/0042315 | A1 * | 2/2011 | Parnas | B01D 61/362 210/640 |
| 2011/0318296 | A1 * | 12/2011 | Braun | A61L 9/05 424/76.1 |
| 2012/0080147 | A1 * | 4/2012 | Offeman | B01D 71/80 156/305 |
| 2012/0080378 | A1 * | 4/2012 | Revanur | B01D 67/0093 210/644 |
| 2012/0280055 | A1 * | 11/2012 | Schneidmiller | A01M 29/12 239/6 |
| 2013/0186974 | A1 * | 7/2013 | Dornau | A61L 2/18 239/34 |
| 2013/0213881 | A1 * | 8/2013 | Diallo | B01D 67/0006 210/500.23 |
| 2013/0292484 | A1 * | 11/2013 | Jackson | A61L 9/14 239/4 |
| 2014/0166774 | A1 * | 6/2014 | Morhain | B32B 25/10 239/34 |
| 2014/0209533 | A1 | 7/2014 | Matviychuk et al. | |
| 2014/0209700 | A1 * | 7/2014 | Olchovy | A61L 9/12 239/34 |
| 2015/0093351 | A1 * | 4/2015 | Horenziak | C11D 3/2093 424/76.1 |
| 2018/0104372 | A1 * | 4/2018 | McGlade | A61L 9/12 |
| 2018/0264413 | A1 * | 9/2018 | Furuno | C02F 1/44 |
| 2019/0307912 | A1 * | 10/2019 | Santini | A01M 1/2088 |

FOREIGN PATENT DOCUMENTS

| | | |
|---|---|---|
| JP | H06219479 A | 8/1994 |
| JP | 2012523302 A | 10/2012 |
| KR | 101364218 B1 | 2/2014 |
| WO | WO9712517 A1 | 4/1997 |
| WO | WO03033039 A1 | 4/2003 |
| WO | WO2008038074 A2 | 4/2008 |
| WO | WO2012050730 A2 | 4/2012 |
| WO | WO2014116470 A1 | 7/2014 |

OTHER PUBLICATIONS

Zhou et al., "PDMS/PVDF composite pervaporation membrane for the separation of dimethyl carbonate from a methanol solution", 2014, Journal of Membrane Science 471(2014) 47-55.

Notification of Reason for Refusal, related Korean Application No. 10-2017-7026090, dated Apr. 26, 2019, 13 pages.

Notification of Reasons for Refusal issued in corresponding Japanese Application No. 2017-549013, dated Dec. 4, 2019, 7 pages.

* cited by examiner

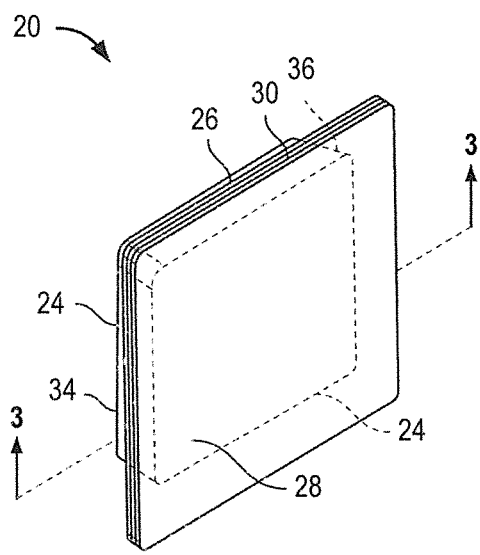
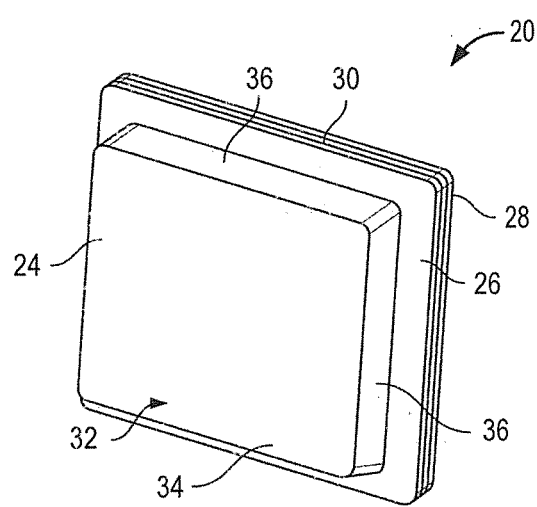
FIG. 1  FIG. 2
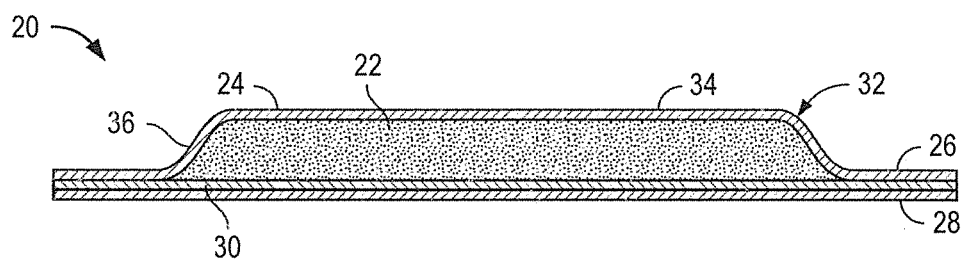
FIG. 3

COMPOSITE MEMBRANE

CROSS REFERENCE TO RELATED APPLICATIONS

This application claims the benefit of priority from U.S. Prov. Pat. App. Ser. Nos. 62/135,359, entitled "Composite Membrane" and filed Mar. 19, 2015, and 62/165,039, entitled "Composite Membrane" and filed May 21, 2015, both of which provisional patent applications are incorporated fully herein by reference.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present invention generally relates to a membrane for transport of a volatile composition and, more particularly, to a composite membrane having a barrier layer and support layer.

2. Description of the Background

The need for effectively combating airborne malodors in various environments (e.g., homes and enclosed public buildings), by odor masking or destruction, is well established, as is the dispensing of pest control materials for killing or deterring insects or other like pests. Various kinds of vapor-dispensing devices or systems have been employed for these purposes. Typical vapor-dispensing devices provide for either the passive or active emission of a volatile composition or material into the atmosphere. Examples of passive dispensers include gel cartridges, potpourri, diffuser systems, aerosols, and the like. By comparison, active vapor-dispensing devices may include fans, heaters, or other actuated dispensing mechanisms that are generally designed to increase the rate of delivery, direct delivery in a particular direction, dispense a vapor on-demand, or a combination thereof.

Currently both passive and active systems may exhibit a number of drawbacks as a plethora of factors may affect the efficacy of a vapor-dispensing device for delivering a fragrance, pest control agent, or other volatile composition. For example, factors such as the overall volume of a space to be treated, the treatment radius (i.e., the linear distance from the vapor-dispensing device), the temperature, humidity, air currents, atmospheric pressure, geographic location, availability of electrical outlets, safety considerations (e.g., presence of small children or pets), and the like may have an affect on the efficacy of a vapor-dispensing device.

Often, a manufacturer of a vapor-dispensing device may offer a wide rage of vapor-dispensing devices in order to provide devices that address the different conditions, environments, and needs encountered by users of such devices. As a result, there is a burden on the manufacturer to invest in the research and development of varied and potentially disparate technologies for vapor-dispensing devices. The manufacturer may then rely on diverse technologies, raw materials, and equipment to produce the membranes, reservoirs, housings, electronics, and the like to produce designed devices.

Given the aforementioned challenges faced by the manufacturers of vapor-dispensing devices, it may be useful to provide for a way to cross-platform normalize, or streamline, the development and manufacture of such devices. Alternatively, (or in addition) it may be useful to provide vapor-dispensing devices that are more versatile or broadly effective in the delivery of fragrances, pest control agents, and the like into an environment.

SUMMARY OF THE INVENTION

According to one embodiment, a refill cartridge for a volatile composition includes a reservoir, a volatile composition within the reservoir, and a composite membrane in fluid communication with the reservoir. The composite membrane includes a barrier layer having a thickness of less than about 10 µm and at least one support layer in contact with the barrier layer, the support layer having a thickness of at least about 10 µm. The volatile composition is transported from the reservoir across the composite membrane at a flux of between 1 and 100 g/(m$^2$·hr) at about 25° C. and about 101 kPa.

According to another embodiment, a refill cartridge for a volatile composition includes a reservoir, a volatile composition within the reservoir, and a composite membrane in fluid communication with the reservoir. The composite membrane includes a first support layer having a thickness of at least about 10 µm, a second support layer having a thickness of at least about 10 µm, and a barrier intermediate the first support layer and the second support layer, the barrier layer having a thickness of less than about 10 µm. The volatile composition is transported from the reservoir across the composite membrane at a flux of between 1 and 100 g/(m$^2$·hr) at about 25° C. and about 101 kPa and comprises a plurality of fragrance molecules. Each of the fragrance molecules is transported from the reservoir across the composite membrane at a flux of at least about 0.006 g/(m$^2$·hr) at about 25° C. and about 101 kPa.

According to a different embodiment, a vapor dispensing device includes a housing, a composite membrane disposed in the housing, and a reservoir disposed in the housing and in fluid communication with the composite membrane. The composite membrane has a barrier layer with a thickness of less than about 10 µm and at least one support layer in contact with the barrier layer, the support layer having a thickness of at least about 10 µm. A volatile composition is provided within the reservoir, wherein the volatile composition is transported from the reservoir across the composite membrane at a flux of between 1 and 100 g/(m$^2$·hr) at about 25° C. and about 101 kPa. Further, the barrier layer is characterized by a low selectivity for transport of the volatile composition.

BRIEF DESCRIPTION OF THE DRAWINGS

Other aspects and advantages of the present invention will become apparent upon reading the following detailed description and upon reference to the drawings in which:

FIG. 1 is a front isometric view of a dispenser including a composite membrane;

FIG. 2 is a rear isometric view of the dispenser of FIG. 1;

FIG. 3 is a cross-sectional view of the dispenser of FIG. 1 along the lines 3-3 of FIG. 1 in a first condition;

DETAILED DESCRIPTION OF THE INVENTION

Figure 4A:
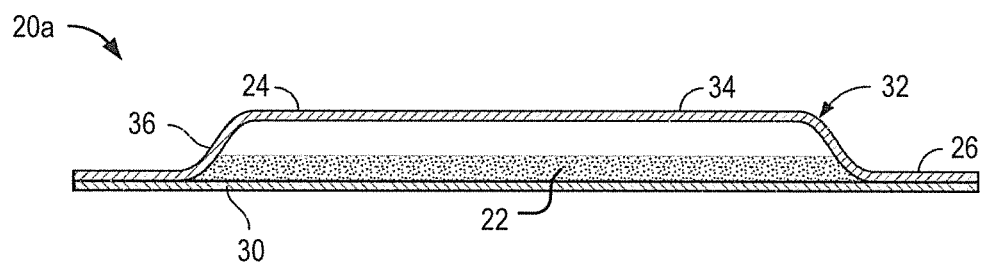
FIG. 4A is a cross-sectional view of an embodiment of the dispenser of FIG. 1, similar to FIG. 3, showing the dispenser in a second condition in which air may enter the reservoir.

In many situations it may be useful to provide a vapor-dispensing device for either the passive or active emission of volatiles into the atmosphere. In one example, it may be useful to emit a fragrance into a space such as a room or household to provide a pleasing aroma. In another example, it may be useful to emit a pest control agent into the atmosphere to repel or eliminate a pest such as a mosquito or other insect. In yet another example, it may be useful to emit a deodorant into an environment in order to neutralize a foul odor or the like. Accordingly, many varieties of vapor-dispensing devices include a reservoir for containing a volatile composition. However, delivery of a volatile composition from the reservoir to the atmosphere may be complicated by one or more factors. For example, active dispensers such as plug-in scented oil (PISO) dispensers typically require a source of energy such as a flame or electricity in order to deliver the volatile material. By comparison, passive dispensers such as gel-based dispensers may not be capable of delivery at high rates on par with active dispensers. Further problems may also arise depending on the type of vapor-dispensing device selected or the environment in which the vapor-dispensing devices is placed. As a result, it may be necessary for a manufacturer of a vapor-dispensing device to invest in the research, development and fabrication of a wide variety of devices. Such an endeavor may be both economically and logistically challenging.

Use of the disclosed examples of a composite membrane or a vapor-dispensing device including a composite membrane may address these and other issues. In one aspect, the present disclosure may provide a versatile composite membrane for use in a wide variety of vapor-dispensing systems. Accordingly, use of the disclosed composite membrane may result in more focused research and development efforts and a more streamlined manufacturing process. Embodiments of a composite membrane may include a barrier layer disposed on a support layer. A barrier layer may be a relatively thin semi-permeable membrane with a thickness of less than about 10 µm (0.00001 m). The barrier layer may be disposed on a relatively thicker porous support layer with a thickness of at least about 10 µm. In other embodiments, a barrier layer may be less than 10 µm and a support layer may be at least 10 µm or greater than 10 µm.

In general, traditional membrane-based volatile delivery systems may include a membrane having a thickness of at least 10 µm. A membrane thickness of at least 10 µm may be required to maintain the mechanical integrity of the membrane as thinner membranes may be too fragile or too easily damaged. However, the surprising discovery has been made that a composite membrane having a barrier layer with a thickness of less than about 10 µm disposed on a relatively thicker support layer may be used for the delivery of a volatile composition in a variety of conditions, including those that exhibit elevated temperatures or a pressure drop across the membrane, as well as other like conditions. Moreover, a composite membrane may be formed with reduced selectivity and increased permeation characteristics as compared with a traditional membrane-based vapor-dispensing device. Accordingly, a volatile material may be delivered to an environment through the membrane without substantially altering the proportions of the individual species included in the volatile composition over time.

In some embodiments, a composite membrane may include a barrier layer configured to be a rate-limiting layer for mass-transport across the composite membrane. That is, for a two layer composite membrane having a barrier layer and a support layer, the barrier layer (and not the support layer) may be rate-limiting for mass-transport across the composite membrane. However, it will be appreciated that embodiments of a composite membrane may have three or more layers, as will be discussed herein. By comparison, the support layer may be configured to be a non-rate-limiting layer, impart mechanical strength to the composite membrane, or a combination thereof. The barrier layer may comprise any suitable material, such as polypropylene, polyethylene, low-density polyethylene, or polydimethylsiloxane (PDMS). Similarly, the support layer may be formed from any relatively porous material (in relation to the barrier layer) such as polyethylene, polyethylene terephthalate, or another polymeric or nonpolymeric porous material.

In some embodiments, a composite membrane may be incorporated into a vapor-dispensing device. An example vapor-dispensing device may include a composite membrane and a reservoir. The reservoir may contain a volatile composition such as a fragrance composition, pest control composition, volatile organic compounds such as aldehydes, alcohols and ketones having from 1-15 carbon atoms per molecule (i.e., $C_1$-$C_{15}$), and the like. For a two-layer composite membrane, the porous support layer may be oriented toward the reservoir and the barrier layer may be oriented toward the environment to which the volatile composition is to be delivered. In some embodiments, the support layer may be near or in communication with, the reservoir in order to wick volatile material toward the barrier layer. By comparison, a three or more layer membrane may also be used. A non-porous barrier layer may be sandwiched between two or more support layers.

In some embodiments, the dispenser may be an active dispenser or a passive dispenser. The vapor-dispensing device may be configured for the delivery of a volatile composition to an environment through the composite membrane at a relatively high rate or flux. In the example case of a passive dispenser, the composite membrane may be configured to transport one or more volatile compounds across the membrane at a rate or flux of up to 6 g/(hr-m$^2$) or more.

One embodiment of a vapor-dispensing device may be a contained (e.g., leak-proof), portable device. The device may be prepared by forming a liquid-tight seal between one or more composite membranes and a reservoir containing one or more volatile compositions. The volatile composition may be delivered across the membrane and into the environment over a period of time. In one aspect, the membrane may be heat sealable with the reservoir. For example, a composite membrane including a non-porous LDPE layer may be heat sealed with a PET reservoir.

In some embodiments, the target delivery rate or flux across the composite membrane may be at least about 5 g/(m$^2$-hr). In other embodiments, the target delivery rate may be at least up to about 10 g/(m$^2$-hr) or more. In yet other embodiments, the target delivery rate may be at least up to about 20 g/(m$^2$-hr) or more. In embodiments in which the vapor-dispensing device is a passive device, the target delivery rate may be achieved at ambient conditions without the need for active temperature or pressure control (e.g., application of heat or vacuum). In addition, the composite membrane may be functional for at least about 30 days without a substantial drop in performance (e.g., due to volatile compounds clogging the pores of the membrane). By comparison, for an active vapor-dispensing device, it may be possible to meet or exceed target delivery rates such as through the use of a fan, a heater, or another active dispensing method.

In one aspect, a composite membrane for use with a vapor-dispensing device may be prepared in any suitable fashion. For example, a composite membrane may be prepared based on methods used for the preparation of composite membranes used in industrial separation systems and processes. It should be noted that while composite membranes have been applied to separation processes in general, the inventors have made the surprising discovery that composite membranes may also be prepared for use in both active and passive vapor-dispensing devices. In one aspect, the discovery was made that embodiments of a composite membrane may be compatible for dispensing or delivering a broad range of compounds. Further, a composite membrane may be used in the fabrication of a vapor-dispensing device for use under varying conditions or in diverse environments.

It will be appreciated that composite membranes for separation processes are generally selective in order to separate one or more species in a mixture. By comparison, a composite membrane according to the present disclosure may be configured to be generally non-selective in the delivery of a volatile composition to an environment. In one example, it may be useful to deliver a composition across the membrane without altering the concentrations of the components of the composition over time. In another example, it may be useful to deliver a broader array of compounds (e.g., varied molecular weight, hydrophobicity, polarity, and the like) across a membrane without necessarily excluding components of a composition. Moreover, the composite membrane may be operated under diverse conditions. For example, a passive vapor-dispensing device including a composite membrane may be operated at ambient temperatures and pressures as compared with membranes used for separation processes, which are typically used at elevated temperatures or with a pressure drop across the membrane. However, for other embodiments of a composite membrane, it may be useful to apply heat, light, electrical energy, pressure, vacuum, or another form of chemical, physical, or mechanical energy to actively deliver a composition (i.e., with an active vapor-dispensing device).

As discussed above, composite membranes have been used, in general, for separation processes such as nanofiltration, ultrafiltration, reverse osmosis, pervaporation and the like. However, each of these processes may differ from processes according to the present disclosure. In one aspect, membrane based separations generally rely on selective membranes to exclude portions of a feed composition while allowing a desired species to permeate through the membrane. Selectivity relates to the ability of the membrane to regulate the passage of one or more components of a composition, and flow, which relates to the rate at which a given component passes through the membrane. In one aspect, flow may be referred to in the context of flux (mass transport across the membrane per unit time per unit area), mass loss rate (change in mass of a vapor-dispensing device per unit time), or permeation rate (mass transport across the membrane per unit time). In another aspect, flow may have units of a volume of liquid flowing through the membrane per unit area and per unit time. In some cases, permeabilities may be normalized to the applied pressure.

In another aspect, separation processes are often operated at non-ambient conditions. For example, a pervaporation process may be operated with a significant pressure drop applied across the membrane or at an elevated temperature. While some similarities exist, it may be useful to compare a membrane according to the present disclosure with the aforementioned separation processes to understand the differences between them. Moreover, an understanding of known systems and methods for providing composite membranes for separation processes may inform the selection of a composite membrane according to the present disclosure.

Pervaporation represents a class of continuous processes for separating two or more liquid components through the use of a membrane such as a polymeric or zeolite membrane. Again, this is in contrast to embodiments of composite membranes according to the present disclosure, wherein it may be useful to transport a composition through the composite membrane in a generally non-selective manner. With respect to pervaporation, when the liquid mixture is brought into contact with the membrane, one of the components may be selectively removed from the mixture based on factors such as molecular weight, hydrophobicity, charge, and the like. In general, a pervaporative process may be operated by imposing a pressure drop across the membrane such as by operating under vacuum on the downstream side of the membrane. Moreover, heat may be supplied to the system to further promote evaporative processes or a sweep gas may be provided on the downstream side of the membrane to further promote mass transport processes.

In comparison with processes that may be limited to boiling point separations (i.e., distillation), membrane based separation systems may achieve more complex separations such as for azeotropic mixtures. However, such systems are generally implemented for use where concentrations of the component to be separated are small compared with other components of the mixture. Also, separation membranes are naturally chosen to be selective for the component(s) to be separated. Examples of systems in which membrane-based separation have been applied include organic solvent dehydration, recovery of organic compounds present at low concentrations (e.g., less than about 10%) in water or other aqueous streams, and separation of mixtures of organic compounds.

In another aspect, membrane-based separation processes such as nanofiltration, reverse osmosis, and ultrafiltration are generally performed with a significant pressure drop maintained across the membrane. For example, ultrafiltration may generally take place at pressures from about 100 kPa to about 500 kPa, nanofiltration may generally take place at pressures from about 500 kPa to about 2000 kPa, and reverse osmosis may generally take place at pressures of at least about 1000 kPa. Alternatively, the aforementioned separation processes may be categorized based on the molecular weight cut-off of the membrane. In one aspect, reverse osmosis may be used to prevent the passage of any solute molecule. In another aspect, particles less than about 2 nm may be rejected by nanofiltration membranes. In a further aspect, particles between about 2 nm and about 0.1 mm may be rejected by an ultrafiltration membrane. As in the case of pervaporation, the primary goal of each of these filtration membranes is separation through selectivity.

By contrast, a composite membrane according to the present disclosure may be operated under a variety of conditions. In one aspect, a composite membrane may be operated at ambient conditions. For example, a composite membrane may be operated at about 25° C. and about 100 kPa. Moreover, the pressure drop across the membrane may be minimal. Accordingly, the composite membrane may be tailored for operation at ambient conditions. Alternatively (or in addition), a composite membrane according to the present disclosure may be operated at elevated temperatures, with a pressure drop across the membrane, or a combination thereof.

Further, in some embodiments, the composite membrane may be non-selective for transport of a given volatile composition. The composite membrane may be capable of transporting a wide variety of $C_1$-$C_{15}$ carbon containing molecules such as aldehydes, alcohols, and ketones. The molecules may be transported at generally the same rate such that the proportions of the individual species of the volatile composition in a reservoir are generally maintained without varying over the lifetime of the device, i.e., the composite membrane has a low selectivity as described hereinafter.

With continued reference to composite membranes for separation processes, some membrane-based processes may rely upon the addition or extraction of heat, the application of pressure, or the use of a vacuum. As a result, there is the potential for greater wear on the system due to thermal, chemical, and mechanical effects. Moreover, selective membranes may be prone to fouling as restricted molecules become lodged within the pores of the membrane.

In comparison, the present system may be operated at ambient (or non-ambient) conditions for the generally non-selective (i.e., low selectivity) delivery of a volatile composition to an environment. Accordingly, a membrane according to the present disclosure may, in addition to having advantages over prior art membranes for delivery of a volatile composition, overcome one or more of the challenges associated with selective membranes used for separations. In one aspect, a composite membrane according to the present disclosure may be less prone to fouling due to the non-selective configuration of the membrane. In another aspect, embodiments of a composite membrane may be less prone to wear when operated at ambient temperature or pressures. Still other advantages may be achieved.

In one aspect, the selection of the one or more materials included in a membrane may be based on considerations such as the chemical properties, mechanical properties, thermal stability, manufacturing costs, selectivity, or throughput. For example, it may be useful to include a ceramic material in a composite membrane as ceramic materials may be less susceptible to deformation under pressure or swelling. Moreover, ceramic components may be less resistant to cleaning. However, some ceramic components may be more costly or less mechanically flexible than other materials such as polymers.

In order to select a membrane or combination of membrane layers to form a composite membrane, an understanding of the theory behind mass transport and diffusion may be useful. One proposed mechanism that may be used to model mass transport through a non-porous or semi-permeable membrane (i.e., a barrier layer) is solution-diffusion theory. This theory accounts for processes including upstream absorption into the membrane, diffusion across the membrane, and downstream desorption or evaporation from the membrane. One aspect of solution-diffusion theory includes a partition coefficient, which is defined by Equation 1:

$$\frac{[A_{membrane}]}{[A_{feed}]} = k \qquad \text{(Eq. 1)}$$

where $[A]_{membrane}$ is the concentration of species A in the membrane, $[A]_{feed}$ is the concentration of species A in the feed, and k the partition coefficient, which dependent on the system in question (i.e., the characteristics of the species and the membrane).

In comparison with the partition coefficient, with respect to selectivity or the ability of a membrane to restrict the flow of one or more components of a mixture, a % rejection or molecular weight cut-off may be specified. In one aspect, Equation 2 describes a % rejection for a given membrane:

$$\% \text{ rejection} = \frac{[A]_{feed} - [A]_{permeate}}{[A]_{feed}} \times 100 \qquad \text{(Eq. 2)}$$

where $[A]_{permeate}$ is the concentration of species A in the permeate.

By comparison, the molecular weight cut off may describe the molecular weight at which about 90% of a reference compound is retained or rejected. Each of these parameters may be determined experimentally. By contrast, values found in the literature for various membranes are generally provided for a given set of experimental conditions. As such, it may be difficult to predict the performance characteristics of a membrane when conditions are varied from those reported. By extension, identifying a suitable membrane for a given process may be challenging or unpredictable, which may require screening a number of membranes.

With respect to both selectivity and mass transport, Fick's first law may be used to describe the rate of transport across the membrane:

$$F = D\frac{d[A_{membrane}]}{dx} \quad \text{[Eq. 3]}$$

where F is the permeation flux of species A through the membrane, D is the diffusion coefficient of species A in the membrane, and x is the position of species A in the membrane. Equations 1 and 3 may be combined to describe the upstream and downstream aspects of the transport process as shown in Equation 4:

$$F = Dk\frac{\Delta[A]}{x} \quad \text{(Eq. 4)}$$

where $\Delta A$ is the transmembrane concentration, and D and k are constant. Rearranging equation 4, permeability (P) may be defined as:

$$P = \frac{Fx}{\Delta[A]} = Dk \quad \text{(Eq. 5)}$$

Given the permeabilities of two different components of a composition, the selectivity of a membrane for those two components may be calculated according to Eq. 6:

$$\alpha_{AB} = \frac{P_A}{P_B} \quad \text{(Eq. 6)}$$

where $\alpha_{AB}$ is the selectivity of a given membrane with respect to components A and B, $P_A$ is the permeability of component A for the given membrane, and $P_B$ is the permeability of component B for the given membrane. In general, the greater of the two permeabilities (e.g., $P_A$, $P_B$) may be selected as the numerator in Eq. 6, with the smaller value selected as the denominator such that $\alpha_{AB} \geq 1$. In one aspect, experimental results may be required to calculate the actual selectivity of a given membrane or layer of a composite membrane.

For an ideal separation system, a component A of a mixture may be readily transported across a given membrane, whereas a component B of the mixture may be entirely retained or prevented from crossing the membrane. The permeability of component A in this system may be a larger positive number (i.e., $P_A \gg 0$), whereas the permeability of component B in the idea system approaches zero (i.e., $P_B \approx 0$). The resulting selectivity ($\alpha_{AB}$) approaches infinity as $P_B$ approaches zero. Accordingly, for a system where separation may be desirable, it may be useful to provide a membrane characterized by a large selectivity with respect to the two or more components to be separated. By comparison, for systems configured to transport each of the components of a composition across a membrane at about the same rate, it may be useful to provide a membrane characterized by a selectivity approaching unity (i.e., $\alpha_{AB} \approx 1$). In one aspect, a selectivity approaching unity may result in minimal changes in the concentration of each component within the composition over time.

Solution-diffusion theory may be further modified by taking into account other aspects of the system, such as membrane swelling or plasticization. In one aspect, interactions between the polymer chains of a membrane and solvent molecules may lead to an increase in the free volume, which may in turn lead to an increase in the diffusion coefficient of a given species or multiple species. As a result of these and other membrane-species interactions, additional factors may be taken into consideration. Other aspects of a membrane that may affect mass transport include polar groups in the membrane matrix, membrane hydrophilicity, membrane morphology, the presence or absence of a given functional group, the ion exchange capacity of the membrane, chemical potential, kinetic and thermodynamic transport coupling, and the like. For example, in the case of thermodynamic coupling, the Gibbs free energy of a species may be affected by the surrounding system, thereby resulting in changes in the transport behaviors of the species in the membrane.

In one aspect, it may be useful to select materials for a composite membrane based on factors such as chemical compatibility, mass transport capability, and mechanical integrity. At least one layer of the composite membrane should be compatible with one or more components of the feed solution. Accordingly, it may be useful to consider properties of the membrane such as the solubility of the membrane in the feed solution or the polarity of the membrane. The Hansen solubility parameter may be relied upon for evaluating the degree of selectivity of a membrane for a given volatile mixture or composition. However, knowledge of the atomic or microscale structure of the membrane may be needed to determine a Hansen solubility parameter.

The polarity (or lack thereof) for the components of a composite membrane may further contribute to performance parameters of the membrane. In order to transport a given component of a feed composition across a composite membrane, the polarity of one of the components may be selected to be compatible with the polarity of at least one of the layers of the membrane. In one aspect, the compatibility of a component (i) in a composition to be transported across a membrane with a polymer component in the membrane may be represented by Equation 7:

$$\Delta_{i,polymer} = \sqrt{[(\delta_{d,i} - \delta_{d,polymer})^2 + (\delta_{p,i} - \delta_{p,polymer})^2 + (\delta_{h,i} - \delta_{h,polymer})^2]} \quad \text{(Eq. 7)}$$

where $\Delta$ is the Hansen solubility parameter, $\delta_d$ is the dispersive contribution, $\delta_p$ is the polar contribution, and $\delta_h$ is the hydrogen bonding contribution. Furthermore, i represents a component of the feed composition, which may interact with a polymer associated with one or more layers of the composite membrane. The greater the compatibility between any two components the smaller will be the magnitude of $\Delta$.

In another aspect, it may be useful to consider the Flory-Huggins interaction parameter of a given membrane when determining compatibility with a given feed composition. Turning to Equation 8, the Flory-Huggins interaction parameter may defined as follows:

$$\chi_{i,polymer} = \frac{[\ln(1 - v_{polymer}) + v_{polymer}]}{v_{polymer}^2} \quad \text{(Eq. 8)}$$

where $\chi$ is the Flory-Huggins interaction parameter, $v_{polymer}$ is the volume fraction of the polymer, and i represents the component of the feed solution. For small values of $\chi$ (approaching, but not less than 0.5) the interaction between the component (i) and the polymer generally becomes greater.

In one aspect, equations may be derived for describing these complex transport phenomena. It will be appreciated that as a system becomes more complex with increasing numbers of species, determining the behavior of a given membrane in the presence of a mixture may become increasingly difficult if not impossible to predict.

In light of the challenges associated with predicting the behavior of a given membrane in the presence of a given species or composition, the inventors have determined experimentally that, surprisingly, a composite membrane according to the present disclosure may be compatible for use with a passive or active vapor-dispensing device. Further, embodiments of a composite membrane may be used for the delivery of a composition in a generally non-selective manner. However, it will be appreciated that some embodiments of a composite membrane may further include one or more selective layers as will be discussed herein.

Selectivity relates to a ratio of permeabilities for two different molecules. Accordingly, the selectivity may be defined to be greater than, less than, or equal to 1, depending on the values selected for the numerator and the denominator of Eq. 6. In one example approach, the selectivity of a membrane for two components A and B may be defined to be greater than or equal to 1 (i.e., $\alpha_{AB} \leq 1$). In this case, the component (A or B) having the greater value for permeability will always be selected as the numerator. For example, a first molecule may have a permeability of 10 and a second molecule may have a permeability of 5, each with respect to a given membrane. The selectivity of the given membrane with respect to the two molecules can be calculated as 10 divided by 5, which is equal to 2 (as opposed to 5 divided by 10, which is equal to 0.5 and is less than 1). With respect to the selectivity of a composite membrane (or a layer thereof), a "non-selective" membrane may have a selectivity of about 1 (i.e., $\alpha_{AB} \approx 1$). A generally non-selective membrane or a membrane characterized by low selectivity may have a selectivity of about 1 to about 1000 (i.e., $\alpha_{AB} \leq 1,000$). In another aspect, $\alpha_{AB} \leq 100$ for a membrane characterized by low-selectivity. In yet another aspect, $\alpha_{AB} \leq 50$ for a membrane characterized by low-selectivity. In a further aspect, $\alpha_{AB} \leq 10$ for a membrane characterized by low-selectivity.

In some embodiments, a generally selective membrane or a membrane characterized by high selectivity may have a selectivity of at least about 1,000 (i.e., $\alpha_{AB} \geq 1,000$). In another aspect, $\alpha_{AB} \geq 5,000$ for a selective membrane. In yet another aspect, $\alpha_{AB} \geq 10,000$ for a selective membrane.

In certain aspects, the vapor-dispensing device can provide delivery of the volatile composition across the composite membrane at an initial delivery rate that is measured within one hour of exposing the volatile composition and the composite membrane to the atmosphere. The vapor-dispensing device can provide delivery of the volatile composition across the composite membrane at a subsequent delivery rate that is measured at a fixed time after exposing the volatile composition and the composite membrane to the atmosphere. The fixed time can be any length of time over which the vapor-dispensing device is desired to provide delivery of the volatile composition. For example, the fixed time can be six hours, twelve hours, one day, two days, three days, four days, five days, six days, one week, ten days, two weeks, fifteen days, twenty days, three weeks, twenty-five days, four weeks, thirty days, five weeks, forty days, six weeks, forty-five days, seven weeks, fifty days, fifty-five days, eight weeks, and the like.

It should be appreciated that for the calculations that follow in Equations 9 and 10, the delivery rate can be calculated by any means known to one having ordinary skill in the art, including as a weight loss rate or a flux, because the calculations all have one delivery rate in the numerator and another delivery rate in the denominator, which results in the cancellation of the units. So long as the delivery rate is calculated consistently, the following calculations hold.

In embodiments having a volatile composition with a single component (in other words, a neat volatile composition), one method of measuring the delivery rate for a vapor-dispensing device includes measuring the weight of a vapor-dispensing device at a first time, measuring the mass of a vapor-dispensing device at a second time, optionally measuring the mass of a vapor-dispensing device at a third, fourth, fifth, etc., up to nth time, and fitting the data using a known fitting method, such as a least squares fit.

In embodiments having a heterogeneous volatile composition with at least two components, one method of measuring the delivery rate for a vapor-dispensing device includes the same method described above for use with the single component volatile composition with a further step for differentiating between components. At the same time as the mass is being measured, the gas escaping the vapor-dispensing device can be collected, such as described below with respect to FIG. 7, and the captured gas can be analyzed for relative percent content of individual components, for example, by gas chromatography coupled with mass spectrometry or flame ionization detection. Alternatively, the liquid remaining in the reservoir can be sampled immediately prior to the first mass measurement and immediately after the second mass measurement (note: this sampling can alter the delivery rate of the vapor-dispensing device, so should not be used for a single measurement in a long string of measurements), and processed via gas chromatography-mass spectrometry or liquid chromatography-mass spectrometry to determine the relative concentration of the components. Once the relative concentration of components in the liquid before and after the mass measurements is known, the relative concentration of the gas that escaped can be determined by taking the inverse of the relative concentration of components in the liquid.

As used herein, a rate at a specific time shall refer to the slope of the line fitting the aforementioned mass data at that time. Alternatively, a rate at a specific time shall refer to the mass of the system 150 seconds prior to that time minus the mass of the system 150 seconds subsequent to that time, divided by 300 seconds. Again, for a multi-component composition, the relative concentration of components can be determined as described above.

An initial delivery rate refers to a rate measured within one hour of exposure to the atmosphere. A delivery rate at time t refers to a delivery rate measured at a time t after exposure to the atmosphere.

The vapor-dispensing device can provide a more continuous delivery of the volatile composition when compared with existing delivery systems. This more continuous delivery of the volatile composition can be measured by a delivery continuity factor that can be measured and calculated. The delivery continuity factor is defined as the delivery rate at time t divided by the initial delivery rate. Accordingly, the delivery continuity factor is time-dependent. A total delivery continuity factor is a measurement related to all components of a volatile composition. A component delivery continuity factor is a measurement related to a single component of a volatile composition. A higher delivery continuity factor indicates that the release of the volatile composition is more consistent over time.

The total (T) delivery continuity factor at time t, represented by $^{T}DCF_t$ is calculated by Equation 9:

$$^{T}DCF_t = \frac{^{T}R_t}{^{T}R_i} \quad \text{(Eq. 9)}$$

where $^{T}R_t$ is the total delivery rate at time t and $^{T}R_i$ is the total initial delivery rate.

The individual component (i) delivery continuity factor at time t, represented by $^{i}DCF_t$, is calculated by equation 10:

$$^{i}DCF_t = \frac{^{i}R_t}{^{i}R_i} \quad \text{(Eq. 10)}$$

where $^{i}R_t$ is the delivery rate at time t for individual component i and $^{i}R_i$ is the initial delivery rate for individual component i.

For example, the total delivery continuity factor at a time of one day ($^{T}DCF_{1\ day}$) is the total delivery rate at one day ($^{T}R_{1\ day}$) divided by the total initial delivery rate ($^{T}R_i$).

In certain aspects, the vapor-delivery systems described herein can have a total delivery continuity factor at a time of one day of at least 0.40, at least 0.45, at least 0.50, at least 0.55, at least 0.60, at least 0.65, at least 0.70, at least 0.75, at least 0.80, at least 0.85, at least 0.90, or at least 0.95.

In certain aspects, the vapor-delivery systems described herein can have a total delivery continuity factor at a time of five days of at least 0.35, at least 0.40, at least 0.45, at least 0.50, at least 0.55, at least 0.60, at least 0.65, at least 0.70, or at least 0.75.

In certain aspects, the vapor-delivery systems described herein can have a total delivery continuity factor at a time of ten days of at least 0.30, at least 0.35, at least 0.40, at least 0.45, at least 0.50, at least 0.55, at least 0.60, at least 0.65, at least 0.70, or at least 0.75.

In certain aspects, the vapor-delivery systems described herein can have a total delivery continuity factor at a time of fifteen days of at least 0.25, at least 0.30, at least 0.35, at least 0.40, at least 0.45, at least 0.50, at least 0.55, at least 0.60, at least 0.65, or at least 0.70.

In certain aspects, the vapor-delivery systems described herein can have a total delivery continuity factor at a time of twenty days of at least 0.20, at least 0.25, at least 0.30, at least 0.35, at least 0.40, at least 0.45, at least 0.50, at least 0.55, or at least 0.60.

In certain aspects, the vapor-delivery systems described herein can have a total delivery continuity factor at a time of twenty-five days of at least 0.15, at least 0.20, at least 0.25, at least 0.30, at least 0.35, at least 0.40, at least 0.45, at least 0.50, or at least 0.55.

In certain aspects, the vapor-delivery systems described herein can have a total delivery continuity factor at a time of thirty days of at least 0.10, at least 0.15, at least 0.20, at least 0.25, at least 0.30, at least 0.35, at least 0.40, at least 0.45, or at least 0.50.

In certain aspects, the vapor-delivery systems described herein can have a total delivery continuity factor at a time of fifty days of at least 0.05, at least 0.10, at least 0.15, at least 0.20, at least 0.25, at least 0.30, at least 0.35, at least 0.40, at least 0.45, or at least 0.50.

In certain aspects, the vapor-delivery systems described herein can have an individual component delivery continuity factor at a time of one day of at least 0.40, at least 0.45, at least 0.50, at least 0.55, at least 0.60, at least 0.65, at least 0.70, at least 0.75, at least 0.80, at least 0.85, at least 0.90, or at least 0.95.

In certain aspects, the vapor-delivery systems described herein can have an individual component delivery continuity factor at a time of five days of at least 0.35, at least 0.40, at least 0.45, at least 0.50, at least 0.55, at least 0.60, at least 0.65, at least 0.70, or at least 0.75.

In certain aspects, the vapor-delivery systems described herein can have an individual component delivery continuity factor at a time of ten days of at least 0.30, at least 0.35, at least 0.40, at least 0.45, at least 0.50, at least 0.55, at least 0.60, at least 0.65, at least 0.70, or at least 0.75.

In certain aspects, the vapor-delivery systems described herein can have an individual component delivery continuity factor at a time of fifteen days of at least 0.25, at least 0.30, at least 0.35, at least 0.40, at least 0.45, at least 0.50, at least 0.55, at least 0.60, at least 0.65, or at least 0.70.

In certain aspects, the vapor-delivery systems described herein can have an individual component delivery continuity factor at a time of twenty days of at least 0.20, at least 0.25, at least 0.30, at least 0.35, at least 0.40, at least 0.45, at least 0.50, at least 0.55, or at least 0.60.

In certain aspects, the vapor-delivery systems described herein can have an individual component delivery continuity factor at a time of twenty-five days of at least 0.15, at least 0.20, at least 0.25, at least 0.30, at least 0.35, at least 0.40, at least 0.45, at least 0.50, or at least 0.55.

In certain aspects, the vapor-delivery systems described herein can have an individual component delivery continuity factor at a time of thirty days of at least 0.10, at least 0.15, at least 0.20, at least 0.25, at least 0.30, at least 0.35, at least 0.40, at least 0.45, or at least 0.50.

In certain aspects, the vapor-delivery systems described herein can have an individual component delivery continuity factor at a time of fifty days of at least 0.05, at least 0.10, at least 0.15, at least 0.20, at least 0.25, at least 0.30, at least 0.35, at least 0.40, at least 0.45, or at least 0.50.

In some embodiments, a membrane may include a homogeneous membrane, a composite membrane, or a combination thereof. Furthermore, a membrane may refer to a layer of a membrane such as a barrier layer or a support layer. In one aspect, a homogeneous membrane may be more easily fabricated or integrated into a delivery system. In another aspect, a composite membrane may enable a greater overall flux depending on the construction of the membrane, as in the example case of a composite membrane having a thin homogeneous membrane, active layer, or barrier layer supported on a porous substrate or support layer. In some embodiments, it may be useful to provide a composite membrane having a porous substrate that presents negligible resistance to mass transport. However, a porous substrate having increased resistance may be useful in order to decrease membrane productivity or selectivity (Pinnau, et al. 1991, Ind. Eng. Chem., Res. 30, 1837-1840). Accordingly, it may be useful to consider the compatibility of a support layer with a barrier layer when designing a composite membrane.

Embodiments of a composite membrane may include one or more selective layers. In one aspect, it may be useful to control the delivery of different molecules or compositions based on a configuration of the composite membrane or vapor-dispensing device comprising the composite membrane. For example, a composite membrane may have a removable selective layer. When associated with the composite membrane, the selective layer may limit or prevent the transport of a given subset of molecules within a composition. Accordingly, at least a portion of the composition may not be transported across the composite membrane for delivery to an environment. However, the selective layer may selectively permit at least a portion of the composition to be transported across the composite membrane for delivery to the environment. In some embodiments, the selective layer may be at least partially removed from the composite membrane. For example, the selective membrane may be an exterior layer of the composite membrane that may be configured to be peeled off of the composite membrane. Upon removal of at least a portion of the selective layer, a greater portion of the composition may be transported across the composite membrane due to the removal of the selective layer.

With respect to the overall construction, a composite membrane according to the present disclosure may include a generally planar barrier layer with one or both faces in contact with a porous support layer. In one example, a barrier layer having a thickness dimension of less than about 10 micrometers ($\mu m$) may be layered on (or between) a thicker (e.g., at least about 10 $\mu m$) porous support layer. In another example, a barrier layer may have a thickness dimension of less than about 5 $\mu m$. In yet another example, a barrier layer may have a thickness dimension of less than about 2 $\mu m$. The barrier layers may be cast, glued, fused, clamped, or otherwise applied, mounted, or bonded to a support layer.

The support layer may be thicker than the barrier layer, typically in the range of about 10 $\mu m$ to about 10 mm in thickness. In one example, the support layer has a thickness of about 50 $\mu m$ to about 1000 $\mu m$. In another example, the support layer has a thickness of about 100 $\mu m$ to about 400 $\mu m$. In some embodiments, the support layer may be porous. The support layer may be a backing to the barrier layer that provides mechanical integrity to the composite membrane. The support layer may be a composite of a microporous layer and a nonwoven layer, for example, to provide additional mechanical support. Other layers may also be present, such as a protective topcoat on the barrier layer to protect it from damage or to modify fouling characteristics, an intermediate layer between the barrier layer and the porous support layer to promote compatibility or adhesion between the layers or to improve mass transfer characteristics of the composite membrane, or a combination thereof.

In one aspect, a membrane may be prepared using one or more techniques that are novel or known in the art. One example technique includes phase inversion. Phase inversion is a technique in which the phase transition of a cast polymer film from a liquid to a solid state is carried out in a controlled manner. Phase inversion may be achieved via methods such as immersion precipitation, thermal precipitation, controlled evaporation, and precipitation from the vapor phase. In one aspect, phase inversion may be used to prepare integral asymmetric membranes.

In one aspect, immersion-precipitation techniques may lead to the development of macrovoids, or large tear-drop pores on the order of about 10 $\mu m$ to 50 $\mu m$ that are generally considered to be undesirable in separation applications. In some embodiments, it may be useful to minimize the formation of macrovoids as they may reduce the mechanical integrity of the membrane. In other embodiments, it may be useful to purposefully include macrovoids as a means to configure the mass transport or selectivity characteristics of the membrane. Alternatively (or in addition), it may be useful to form microscale perforations in the membrane to tailor the mass transport characteristics of the membrane.

Examples of suitable polymers for the preparation of membranes via immersion-precipitation include polyacrylonitriles, polyvinylidene fluorides, polyimides (e.g., MATRIMID, LENSING P84), polyetherimides, polyamides, polyamide hydrazides, polysulfones, polyethersulfones, polyether ether ketone, sulfonated polyether ether ketone, polyphthalazinone ether sulfone ketone, sulfonated polyphthalazinone ether sulfone ketone, cellulose acetate, and polybenzimidazole.

Still other techniques may be used to prepare composite membranes. For example, a composite membrane may be formed using a thin film or ultra thin film process (see, e.g., Petersen, et al. 1993, J. Membr. Sci., 83, 81). A thin film composite membrane may include an ultra-thin (submicron) separating barrier on top of a chemically different porous support. Thin film composite membranes may be prepared using techniques such as dip-coating or interfacial polymerization. In the case of the latter method, a support layer may first be prepared, such as by phase inversion followed by coupling of the support laser to the barrier layer. In one aspect, it may be useful to form a composite membrane where each of the support layer and the barrier layer are individually selected based on the application.

In one aspect, a membrane may include structural elements, such as aromatic groups, imide bonds, or halogen groups. The use of such structural elements may be used to tailor the solvent stability of the membrane. In another aspect, co-polymerization, which may result in a more rigid membrane, may be carried out in order to further impart solvent resistance.

In one aspect, a membrane may be formed from a composition including a solvent and one or more additives. In one aspect, volatile solvents such as tetrahydrofuran or 1,4-dioxane or non-solvent additives may be included in a casting solution for a membrane to manipulate the selectivity of the resulting membrane. Moreover, non-solvent additives may be used to control the formation of macrovoids.

In some embodiments, it may be useful to control the formation of pores within a membrane. For example, it may be useful to control the number, distribution, concentration, or dimensions of the pores of one or more layers of a composite membrane. Examples of materials that may be used to prepare or control the formation of pores (i.e., pore-forming additives) include inorganic salts, such as LiCl and $LiNO3$, $Mg(ClO_4)_2$, and organic materials such as poly(ethylene glycol) and polyvinylpyrrolidone. In the case of the organic pore-forming additives, the molecular weight of the additive may also have an affect on the structural nature of the membrane, such as the degree of porosity. Other techniques that may be used to affect the properties of a membrane during casting include controlling the rate of solvent evaporation or the inclusion of a chemical-, plasma-, or photo-induced cross-linking step.

In some embodiments, interfacial polymerization may be used to prepare a barrier layer of a composite membrane. Interfacial polymerization may include the coupling of a barrier layer with a porous support layer through a polymerization reaction at the interface between two layers.

In some embodiments, a membrane may be prepared by solvent-casting, wherein a coating of a polymer solution is applied to a support material. In one aspect, the viscosity of the casting solution may be tailored to achieve a given amount of intrusion of the cast material into the pores of the support material.

In some embodiments, modifications may be made to one or more polymer components for tuning the mass transport properties of a membrane according to the present disclosure. In one aspect, cross-linking of a polymer may decrease the solubility of a feed composition in the polymer. In another aspect, cross-linking may lead to decreased swelling during use of the membrane, thereby affecting the selectivity of the membrane. Examples of cross-linking include the formation of covalent bonds through chemical reaction or irradiation, and physical cross-linking (e.g., the formation of physical interactions or entanglement). However, the degree of cross-linking may affect the mechanical properties of the polymer (e.g., brittleness vs. elasticity).

In other embodiments, it may be useful to use one or more grafting techniques for preparing a composite membrane. For example, oligomeric side-chains may be covalently grafted to a main polymer chain at regular or irregular intervals through processes such as chemical reaction or irradiation. In one aspect, the use of a primary polymer chain having one or more reactive functional groups may provide a location for grafting to take place. Primary polymers that may be used as a starting point for grafting procedures include polyvinylidene difluoride, polyvinyl fluoride, and polytetrafluoroethylene. Examples of oligomers and other materials that may be grafted may include N-vinylpyrrolidone, 4-vinylpyridine, vinyl acetate, acrylic acid, and N-vinylimidazole.

Other techniques for preparing polymer membranes may include blending. In one aspect, blending of two or more polymer materials may be used to tune the degree of hydrophobicity or another property of the resulting polymer blend. For example, a hydrophilic polymer may be combined with a hydrophobic polymer in varying ratios. The resulting compositions (blends) may then be analyzed to determine characteristics such as the permeability or selectivity. The selection of the polymers to be included in a blend may be varied in order to provide a homogeneous or heterogeneous blend. For example, a homogenous blend may include two polymers, which are miscible with one another at the molecular level. A heterogeneous blend may include two or more polymers, which are at least partially immiscible at the molecular level. Examples of heterogeneous blends may share similarities with block copolymers, which are described hereinafter. As compared with grafting and other polymer formation techniques, blending may have an impact on the mechanical characteristics of the polymer membranes or the constituent layers.

In comparison with blending, a covalent bond may be formed between two or more polymers. In one aspect, forming a covalent bond between the two or more polymers may affect the mechanical properties of the membrane. Examples of covalently bonded polymers include graft, block, and random copolymers. In general, graft copolymers may be generally crystalline in nature. By contrast to membranes used for pervaporation or other separation oriented processes, membranes including random copolymers may be used without the need for a minimum amount of crystallinity in embodiments where a non-selective membrane may be useful. It will be appreciated that the use of the aforementioned techniques may not be mutually exclusive. Accordingly, the formation of polymer compositions may include the use of two or more of the aforementioned techniques.

In general, membranes may be formed from polymers, ceramics, wovens, nonwovens, zeolites and the like, and combinations thereof. Moreover, a membrane may be homogeneous, heterogeneous, symmetric, asymmetric or a composite membrane. An asymmetric membrane may include a thin dense layer on top of a porous support layer of the same material. In one aspect, an asymmetric membrane may be prepared using techniques such as phase inversion (see, e.g., U.S. Pat. No. 5,708,040 to Hong et al.). By comparison, composite membranes may include a support layer with a barrier layer disposed on top of it. In one aspect, the barrier layer may be formed from a material that is different from the support layer.

In some embodiments, a membrane may include one or more ceramic materials or layers. Ceramic membranes may be useful as ceramic fibers (or other materials) may impart greater thermal stability to the membrane as compared with other materials that may be more susceptible to thermal degradation or alteration. Example ceramic materials may include aluminum oxide, silicon oxide, titanium oxide, and zirconium oxide. Barrier layers for use with ceramic membranes may be prepared via a sol-gel synthesis method.

In some embodiments, the barrier layer may be a polymer, copolymer, or blend of polymers. It may also have a mixed matrix composition, wherein small solid particles are embedded within a continuous polymer matrix. The barrier layer may also contain other additives to modify the selectivity, permeability, physical properties of the membrane, or aid in its formation. Additives may include, but are not limited to, adsorbents such as zeolites (e.g., ZSM-5 and USY) or other molecular sieves, filler particles (e.g. fumed silica, carbon black), plasticizers, surfactants, and stabilizers. The thickness of the barrier layer may also be minimized to achieve high flux rates of 800-5000 $g/m^2$ hr with barrier layer thicknesses of about 1 µm to about 10 µm.

The barrier layer may optionally comprise hydrophobic filler(s), e.g., absorbents capable of absorbing volatile organic compounds intended to be separated from the solution. The hydrophobic filler(s) can be present in the selective layer in an amount of 1 wt % to 25 wt %, based upon a total weight of the selective layer. Alternatively (or in addition), a molecular sieve such as activated carbon, silicalite, or other hydrophobic adsorbents may be used. Example absorbents may include hydrophobic adsorbents such as carbonaceous adsorbents made by polymer pyrolysis, hydrophobic inorganic adsorbents having a high surface area such as hydrophobic zeolite-based adsorbents, hydrophobic molecular sieves, hydrophobic polymer resin adsorbents, and the like, as well as combinations comprising at least one of the foregoing. Some exemplary hydrophobic absorbents are disclosed in U.S. Pat. No. 6,117,328 to Sikdar et al. and U.S. Pat. No. 5,755,967 to Meagher et al.

In some embodiments, a support layer may include one or more layers. For example, the support layer may be homogenous (i.e., having a single layer) or a composite membrane itself including two or more layers. Alternatively (or in addition), a composite membrane may include two or more distinct support layers. Further, it may be useful to select a support layer based on the desired or required structural integrity of the composite membrane. A support layer may be selected to provide mechanical stability or otherwise support a barrier layer. In another aspect, a support layer may function as a wicking layer or otherwise enhance the transport of a feed composition toward or away from a barrier layer. In comparison with the barrier layer, factors that may influence the selection of a support layer may include mechanical, chemical, or thermal properties of the support layer material(s). The surface characteristics may also contribute to the ability of the support layer to interface with a barrier layer. For example, the roughness or polarity of the surface of the support layer may influence the ability of the barrier layer to adhere to, bond with, or otherwise couple to the barrier layer. Further characteristics of the support layer that may influence the adhesion of the cast material include surface roughness, porosity, and hydrophilicity.

In some embodiments, a membrane may include a support layer such as a polyester or polypropylene/polyethylene nonwoven backing. A support layer may be included, for example, to improve the mechanical strength or the ability to manipulate the membrane during or after fabrication. Other suitable support layer materials include asymmetric microporous polysulfone, polyether sulfone, polyacrylonitrile, polyvinylidene fluoride and polypropylene, polyimides, polybenzimidazole, inorganic materials, or combinations thereof. Further examples of support layers are described in U.S. Pat. No. 6,986,844 to Barss et al. and U.S. Pat. No. 5,266,207 to Boye et al.

In some embodiments, the support layer may have a flow resistance that is relatively small compared to the barrier layer. For example, the support layer may be configured to be a relatively open, porous substrate. However, in other embodiments, the support layer may have a flow resistance that is relatively equal or greater than the flow resistance of the barrier layer. The support layer may be an inert material. Moreover, while a membrane may be operated at ambient conditions for the delivery of a volatile composition, if a pressure drop is imposed, a support layer may be configured to have sufficient structural integrity to support one or more other layers of the membrane under the stress of the imposed pressure gradient. Further materials that may be included in a support layer include metals, glass, graphite, polymeric materials, ceramic materials, and combinations thereof.

Yet other examples of suitable polymeric materials for preparing a support layer include polysulfone, polyimide, polyvinylidene fluoride, polyamide, polyolefins, polyethylene, polytetrafluoroethylene, polyphenylene, polyphenylene sulfide, polypropylene, fluorinated polyolefins, polytrimethylpentene, polyvinylidene difluoride, and combinations thereof. Examples of suitable ceramic materials for preparing a support layer include silica, zirconia, alumina, inorganic oxide supports, functionalized inorganic oxide supports, and combinations thereof. Examples of suitable metals for preparing a support layer include zinc, titanium, and combinations thereof. Examples of suitable metal alloys for preparing a support layer include brass, stainless steel, and the like. Further support materials that may be suitable are disclosed in U.S. Pat. No. 6,440,309 to Cohen and U.S. Pat. No. 5,334,314 to Neel et al.

In one aspect, a composite membrane may be exposed to an amount of swelling during operation. In another aspect, a composite membrane may be exposed to hot or cold temperatures during operation. If the barrier layer and the support layer do not swell in a coordinated manner, a large stress may be produced at the interface(s) between the components of the composite membrane. Accordingly, it may be useful to tune the compatibility of layers of a composite membrane such as a support layer, barrier layer, or other layer.

Improving the structural stability of a composite membrane may be achieved through one or more of several possible approaches, such as cross-linking, using a multilayer structure (see, e.g., U.S. Pat. No. 4,602,922 to Cabasso et al. or U.S. Pat. No. 5,286,280 to Chiou et al.), or an asymmetric membrane structure. Further methods are described by Shao and coworkers (Shao, et al. 2007, J. Membrane Sci., 287, 162-179). It may also be possible to accommodate for swelling of the membrane while in contact with the feed solution. For example, it may be useful to control the degree of cross-linking within a given layer of a composite membrane, or between layers of a composite membrane. Examples of physical cross-linking are described in U.S. Pat. No. 4,929,358 to Koenitzer.

In some embodiments, the degree of cross-linking of a polymer membrane may be optimized to provide high throughput with low selectivity for a variety of volatile compounds. In another aspect, cross-linking may be varied to control the degree to which the one or more layers of the composite membrane swell when in contact with the volatile material. In a further example, a swellable polymer such as PDMS may be coated onto the surface of the pore walls of the support layer. When in contact with a compound for transport across the membrane, the PDMS may swell, thereby occluding the pores to prevent leakage while also functioning as a diffusion membrane.

In another aspect, it may be useful to provide a highly crystalline polymer, which may not be readily soluble in the presence of volatile organic compounds such as fragrances or insecticides. Other polymer compositions which may limit the degree of swelling may be useful for lowering permeability as compared with polymers that are more amorphous in nature. The degree of crystallinity may also affect the dissolution of the feed mixture in the membrane, thereby limiting swelling or regulating transport through the membrane. Examples of crystalline polymers include polyvinylidene difluoride, low or high density polyethylene, polypropylene, and polystyrene. In one aspect, the absence of polar groups may enable the polymer to absorb volatile organic compounds present in the feed composition. However, such polymers may selectively absorb such organic compounds over more hydrophilic or aqueous materials such as water, or organic compounds such as methanol or benzene. Elastomers such as nitrile rubber membranes may also be useful for inclusion in the design of a composite membrane.

In one aspect, it may be useful to form an interpenetrating layer of the barrier layer with the pores of the support layer. However, the degree of interpenetration may have an affect on the mass transport characteristics of the membrane. Accordingly, it may be useful to optimize the degree of interpenetration.

In one aspect, a membrane conditioning step may be implemented following synthesis or fabrication of the membrane, but preceding use of the membrane in the selected process. For example, a membrane may be maintained in a storage solution prior to use. Thereafter, the membrane may be conditioned prior to use such as through removal of the storage solution by rinsing. Notably, if a conditioning step is not sufficient to prepare the membrane for use, performance of the membrane may be diminished. It will be appreciated that appropriate storage and rinsing conditions may need to be experimentally determined and may vary depending on the membrane, storage conditions, use conditions, or combinations thereof.

Examples of storage conditions may include the storage of the membrane in a solution in order to fill the pores of the membrane with the storage composition. In one aspect, the pores of the membrane may collapse due to capillary forces if allowed to dry out. As the nature of the pores of the membrane may contribute to characteristics of the membrane such as throughput and selectivity, it may be useful to consider storage and preparation of the membrane. In one aspect, a storage solution may include a conditioning agent. Examples of suitable conditioning agents include lubricants such as oil and glycerol. The storage solution may further include a solvent, such as an organic or aqueous solution. In one aspect, the solvent may be selected based on the ultimate use of the membrane. For example, if a membrane is to be used to deliver an organic solution, it may be useful to store the membrane in a storage solution including an organic component.

In another aspect, application of a conditioning agent to a membrane may enable storage of the membrane in the absence of a storage solution or other liquid material. Accordingly, it may be possible to store the membrane in a dry or semi-dry state. In one example, the application of a lubricant to the pores of a membrane may prevent the pores from collapsing in the absence of a liquid media. In order to avoid pore obstructions and concomitant lowered fluxes, the conditioner should obviously be removed carefully with an appropriate solvent prior to application. Once the conditioning agent has been removed, the membranes should never be left dry without re-introduction of the conditioner. Generally, membranes with a dense rubbery top-layer supported by a layer with sufficiently large surface pores may be stored dry without many precautions. Further details related to pore protection may be found in U.S. Pat. No. 5,265,734 to Linder et al.

In some embodiments, membranes may undergo a post-treatment step. Examples of suitable post-treatments include grafting, curing, plasma, UV, and chemical treatments. Such post-treatment steps, may, for example, be used to alter the mass transport properties of the membrane. Alternatively (or in addition), a coating may be applied as a post-treatment step. Suitable coating materials for the preparation of composite membranes may include PDMS, polyether imide, poly(2,6-dimethyl-1,4-phenylene oxide), polyvinyl alcohol, chitosan and other cellulose derivatives, polyether-b-amide, polyacrylic acid, polyphosphazene, polyaliphatic terpenes, poly[1-(trimethylsilyl)-1-propyne], polyurethanes, and combinations thereof.

In some embodiments, a membrane may be incorporated into a module. One example of a module includes a membrane and a housing for supporting or containing the membrane. A membrane may take on a particular configuration such as a flat sheet or cylindrical shape. Accordingly, the overall geometry of the module may be at least partially influenced by the configuration of the membrane. In one aspect, selection of a membrane geometry of a module may influence the compactness of the system. A vapor-dispensing device may include one or more modules. In one embodiment, a module may include a membrane having a flat sheet configuration. The module may further include a reservoir or define a reservoir with the membrane. The module may further be insertable within a housing. Alternatively, the module may include or define a housing.

In some embodiments, a membrane may be formed as a tubular module. For example, a tubular membrane may be generally cylindrical in shape with a support or mechanical layer formed about the outside of the cylindrical membrane. In one aspect, a tubular membrane module may include a porous layer positioned between the support tube and the membrane. In another aspect, a tubular module may include two or more concentric membrane layers. In the case of a module including multiple membranes, porous layers may be positioned between each of the layers.

In some embodiments, a membrane may be formed as a capillary module. For example, a capillary module may include an arrangement or bundle of capillary fibers. The fibers may be positioned in a parallel or intertwined manner. Moreover, one or both of the ends of each fiber may be coupled to a head plate. In one aspect, the high packing density of a capillary module may provide increased resistance to mass transport, which may result in a lower mass loss rate or flux as compared with other module designs.

In some embodiments, a membrane may be formed as a hollow fiber module. For example, a hollow fiber module may include one or more cylindrical fibers with hollow centers. The fibers may be positioned in a container or housing. Furthermore, similar to the capillary module, one or both of the ends of each fiber may be coupled to a head plate. A feed composition may be provided at one end of the housing such that it may flow radially or parallel to the hollow fibers. In one aspect, a hollow fiber module may enable a higher packing density as compared with other module designs.

In some embodiments, a membrane may be formed as a plate and frame system, such as that described in U.S. Pat. Pub. 2002/0038782 to Kim et al. In other embodiments, a membrane may be formed as a spiral wound module (see, e.g., U.S. Pat. No. 4,033,878 to Foreman et al.). In the case of a spiral membrane, the feed composition may enter the membrane along an axial flow path. Thereafter, the permeate may exit the membrane in a radial direction.

In one aspect, the configuration of a membrane or vapor-dispensing device may be varied to achieve a given objective. For example, the configuration may be used to control the rate of delivery, the format or form factor of the vapor-dispensing device, or other factors. The selection of a particular configuration may further depend on factors such as the number and geometry of the membranes, capital and manufacturing costs, ability to clean or replace the membrane or a cartridge or module including the membrane, and the like.

In one aspect, it may be useful to provide a composite membrane for delivering a volatile composition at a given rate. For example, the surprising discovery has been made that embodiments of a composite membrane may be able to deliver a volatile composition to an environment at a rate of at least about 30 g/(m$^2$ hr). However, it may be useful to provide a membrane that can deliver a volatile composition to an environment at a greater or lesser rate. In order to control the delivery rate of a volatile composition, one of several approaches may be taken.

With respect to the barrier layer of a composite membrane, properties that may be manipulated to regulate a delivery rate may include pore size, tortuosity, thickness, hydrophobicity, and the like. In one example, pore size may be increased to increase the delivery rate or decreased to in order to reduce the delivery rate. In another example, the tortuosity of the barrier layer or the thickness of the barrier layer may be increased in order to reduce the delivery rate. In a further example, the hydrophobicity or other chemical properties of the barrier layer may be selected based on the chemical properties of a volatile composition in order to alter the delivery rate. In the example case of a polyethylene barrier layer, a hydrophobic composition may cross the barrier layer more readily than a relatively more hydrophilic composition. A non-aqueous volatile composition including hydrocarbons species such as alkanes, alkenes, alkynes, the like, or combinations thereof may be generally considered to be a hydrophobic composition. By comparison, an aqueous composition or a volatile composition including hydrocarbon species such as alcohols, esters, carboxylic acids, the like, or combinations thereof, may be a relatively more hydrophilic composition. Accordingly, the hydrophobicity of the barrier layer may be selected based on the hydrophobicity of the composition to be delivered across the barrier layer. Fine tuning of the hydrophobicity of the barrier layer may be achieved by varying the composition of the barrier layer, functionalization of the barrier layer, or by other known techniques.

Alternatively (or in addition), it may be possible to alter the properties of the volatile composition given a particular barrier layer. For example, it may be possible to formulate a composition based on a given barrier layer and a desired performance. To increase the rate at which a composition is delivered across a hydrophobic membrane, it may be useful to select a volatile composition with hydrophobic components. Further, it may be possible to modify the chemical structure of a given component to alter properties such as hydrophobicity or molecular weight to increase or decrease the rate at which the component is transported across the membrane. In another aspect, the relative concentration of a component may be varied. Other modifications to a given volatile composition may also be made without departing from the scope of the present disclosure.

In some embodiments, the support layer of a composite membrane may be modified in order to manipulate the delivery rate of the overall membrane for a given volatile composition. As in the case of the barrier layer, aspects of the support layer that may be manipulated to regulate a delivery rate may include pore size, tortuosity, thickness, hydrophobicity, and the like. In one aspect, each of the aforementioned techniques for altering the properties of a barrier layer may be applied to a support layer of a composite membrane. The properties of the support layer may be further modified to match the properties of the barrier layer. Accordingly, a support layer and a barrier layer may be simultaneously modified or configured to achieve a given delivery rate.

In another aspect, a support layer may provide improved mechanical strength without being rate-limiting for transport across the composite membrane. By comparison, a monolayer or non-composite membrane may be made thicker to achieve greater mechanical strength, which may lead to a reduction in the flux of the monolayer membrane.

One embodiment of a vapor-dispensing device or dispenser 20 for emitting a volatile material 22 is illustrated in FIGS. 1-4B. With reference to FIGS. 1 and 2, the dispenser 20 or cartridge comprises a blister 24, a peripheral flange 26, and an impermeable laminate 28 releasably adhered to the blister 24 and the flange 26. The blister 24 includes a composite membrane 30 and a cup-shaped structure 32 or reservoir. The cup-shaped structure 32 includes a bottom wall 34 and four side walls 36 that in conjunction with the composite membrane 30 act as a sealed reservoir to contain the volatile material 22 (shown in FIGS. 1 and 2). Illustratively, the cup-shaped structure 32 and the composite membrane 30 are formed from clear and/or translucent materials, thereby allowing the volatile material 22 to be visible therethrough. The peripheral flange 26 is planar and is coupled to and extends outwardly from top edges of the cup-shaped structure 32. In one embodiment, the peripheral flange 26 extends outwardly from upper edges of the side walls 36 and is integrally formed therewith.

FIG. 1 illustrates the dispenser 20 in a first condition. The dispenser 20 is completely or substantially full in the first condition, i.e., little or no volatile material 22 has diffused through the composite membrane 30 because the impermeable laminate 28 has not been removed from the blister 24. There is substantially no diffusion of the volatile material 22 when the dispenser 20 is filled and the impermeable laminate 28 covers the composite membrane 30. Illustratively, the impermeable laminate 28 is removed from the blister 24 by a user grasping an end of the impermeable laminate 28 and peeling it off the blister 24. A tab, extension, or other means for grasping may be included as an extension of the impermeable laminate 28 to aid in removal of same. The extension may be at the corners, ends, and/or on the surface of the impermeable laminate 28.

Figure 4B:
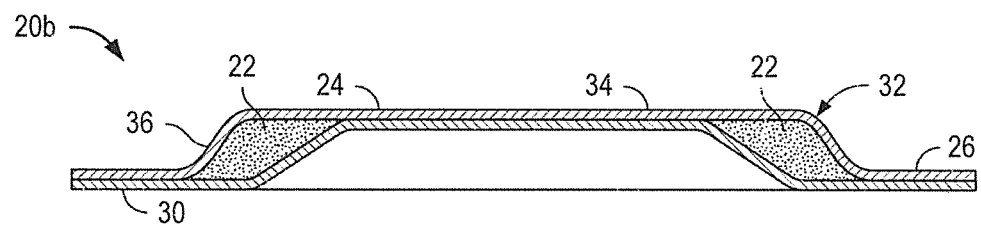
FIG. 4B is a cross-sectional view of the dispenser of FIG. 1, similar to FIG. 3, showing the dispenser in a second condition in which air may not enter the reservoir.

Following removal of the impermeable laminate 28, the dispenser 20 begins to transition from a full or first condition (FIG. 3) to an empty or second condition (FIG. 4A or 4B). There may be a small amount of the volatile material 22 that remains in the blister 24 and the dispenser 20 will still be considered to have reached the second condition. With reference to the dispenser 20a of FIG. 4A, following diffusion of the volatile material 22 across the composite membrane 30 there is less volatile material 22 contained within the dispenser 20. Air may enter the dispenser 20 subsequent to diffusion of the volatile material 22 in order to maintain equilibrium (i.e., a negligible pressure drop exists across the membrane). In one aspect, the lack of a pressure gradient enables the dispenser 20a and composite membrane 30 to retain a general shape with respect to the first condition of the dispenser 20 as shown in FIG. 3.

Depending on the nature of the volatile material 22, the orientation of the dispenser 20a may at least partially affect the degree of contact between volatile material 22 and the composite membrane 30. For example, in the orientation shown in FIG. 4A, the dispenser 20a is generally horizontal with the composite membrane 30 oriented downwards. Accordingly, if the volatile material 22 is capable of flowing, the volatile material 22 may form as a layer disposed on the composite membrane 30. By extension, if the dispenser 20a were to be rotated 90 degrees such that the composite membrane 30 is oriented to one side, the volatile material 22 may flow toward a side wall 36 of the dispenser 20a. As a result, only a portion of the composite membrane 30 may be in contact with the volatile material 22. In one aspect, the orientation of the dispenser 20a (or another dispenser) may affect the degree of contact between the composite membrane 30 and the volatile material 22, and therefore possibly also the flux of the volatile material 22 across the composite membrane 30.

Turning to FIG. 4B, in a second embodiment, as the volatile material 34 diffuses through the composite membrane 26, the composite membrane 26 slowly collapses upon the bottom wall 30. Following diffusion of the volatile material 22 across the composite membrane 30 there is less volatile material 22 contained within the dispenser 20. Substantially no new air enters the dispenser 20 subsequent to diffusion of the volatile material 22. The result of this is a pressure gradient across the composite membrane 30, with a higher pressure existing in the ambient air than the pressure in the dispenser 20. The pressure gradient causes the ambient air to exert a net positive pressure upon the dispenser 20, which presses the composite membrane 30 against the remaining volatile material 22 and ultimately the bottom wall 34.

The volatile material 22 may include a fragrance, an insecticide, a deodorizer, a fungicide, a bacteriocide, a sanitizer, a pet barrier, or other active volatile or other compound disposed within a carrier liquid (for example, an oil-based and/or water-based carrier), a deodorizing liquid, or the like. Examples of possible insecticides include metafluthrin and transfluthrin, among others. Additional examples of the volatile material 22 include OUST™, an air and carpet sanitizer for household, commercial, and institutional use, or GLADE®, a household deodorant, both sold by S. C. Johnson and Son, Inc., of Racine, Wis. The volatile material 22 may also comprise other actives, such as sanitizers, air and/or fabric fresheners, cleaners, odor eliminators, mold or mildew inhibitors, insect repellents, and the like, or others that have aromatherapeutic properties. The volatile material 22 alternatively comprises any fluid known to those skilled in the art that can be dispensed from a container, such as those suitable for dispersal in the form of particles or droplets suspended within a gas and/or propelled by means of a propellant. In one example, a vapor may be formed, dispensed into (e.g., with a propellant), or otherwise provided in a reservoir or chamber in fluid communication with a composite membrane. Thereafter, one or more species within the vapor may be transported across the composite membrane and into an environment. In another example, particles or droplets suspended within a gas and/or propelled by means of a propellant may be applied to one or more surfaces of a composite membrane for transport across the membrane and into an environment. The dispenser 20 is therefore adapted to dispense any number of different fluid or product formulations.

In one aspect, a volatile material may include one or more natural or synthetic fragrance molecules. In some embodiments, the volatile material may be a composition including ten or more fragrance molecules. However, the range of fragrance molecules included in a volatile material may vary. In some embodiments, the molecular weight of a fragrance molecule may be between about 150 and about 300, although fragrance molecules having larger or smaller molecular weights may be suitably incorporated into a fragrance composition.

In general, fragrance molecules can include natural or synthetic aldehydes, ketones, esters, alcohols, terpenes, natural botanic extracts, essences, fragrance oils, and the like. Example oils and extracts that may be derived from plants include almond, *Amyris, anise*, armoise, bergamot, bitter orange, *Cabreuva, Calendula*, canaga, caraway, cedar, chamomile, clove, coconut, *eucalyptus*, fennel, *Geranium*, jasmine, *juniper*, lavandin, lavender, lemon, *mandarin* orange, neroli, orange, *origanum, palm*, patchouli, peppermint, petitgrain, *Quassia*, rose absolute, rosemary, thyme, and the like. Further fragrance molecules that may be derived from floral materials and fruits include dimyrcetol, phenylethyl alcohol and tetrahydromuguol, decyl aldehyde, undecyl aldehyde, undecylenic aldehyde, lauric aldehyde, amyl cinnamic aldehyde, ethylmethyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, parahydroxyphenolbutanone, 6-acetyl-1,1,3,4,4,6-hexamethyl tetrahydronaphthalene, alpha-methyl ionone, gamma-methyl ion-one, and amyl-cyclohexanone and mixtures thereof. Additionally (or alternatively), a volatile material may include or be combined with other molecules and compositions such as a volatile pesticide or a therapeutic agent (e.g., menthol). Further discussion of suitable fragrance molecules for providing a volatile material is found in U.S. Pat. No. 8,778,860 to Saint Victor, U.S. Pat. No. 8,662,409 to Tasz et al., EP Pat. No. 912,200 to Martin et al., and WO 1998/026809 to Martin et al.

In some embodiments, a volatile material may be a scented oil. In general, a scented oil can include woody or earthy bases such as sandalwood oil, civet, patchouli oil, and the like. Other scented oils may have a light floral fragrance, such as rose extract or violet extract. Scented oil may further be formulated to provide desirable fruity scents, such as lime, lemon, or orange. Examples of synthetic fragrance compositions either alone or in combination with natural oils are described in U.S. Pat. No. 4,314,915 to Wiegers et al., U.S. Pat. No. 4,411,829 to Schulte-Elte et al., and U.S. Pat. No. 4,434,306 to Kobayashi et al. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

In some embodiments a volatile material may be provided as a crystalline solid. In one aspect, the crystalline solid may be formulated to sublime into the vapor phase at ambient temperatures. A crystalline fragrance starting material may be selected from organic compounds which include vanillin, ethylvanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, proeugenol acetate, evernyl, and the like.

In some embodiments, the volatile material may include or be combined with a carrier composition such as a solid, liquid, gel, or a combination thereof. A carrier composition may include both fragrance molecules and non-fragrance molecules. In one aspect, a carrier composition may be provided as a gel such as a carrageenan gel, a guar-based gel, a polyacrylate gel, the like, or a combination thereof. Example gels are further described in U.S. Pat. No. 2,927,055 to Lanzet, U.S. Pat. No. 5,741,482 to Modi, U.S. Pat. No. 7,138,367 to Hurry et al., and WO 1998/019717 to Modi. Another example carrier may include a liquid carrier. In one aspect, the liquid carrier may have a density or hyrdrophobicity so as to be immiscible with the fragrance composition or another carrier composition. In other embodiments, a carrier composition may include a solid carrier matrix, such as a porous solid material or sponges. Further, combinations of different types of carriers within a single dispensing device are also contemplated.

Figure 5:
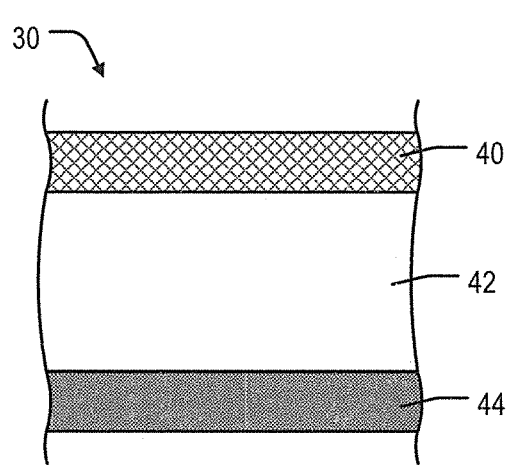
FIG. 5 is a partial sectional view of an embodiment of a composite membrane including a barrier layer and a support layer.
Figure 6:
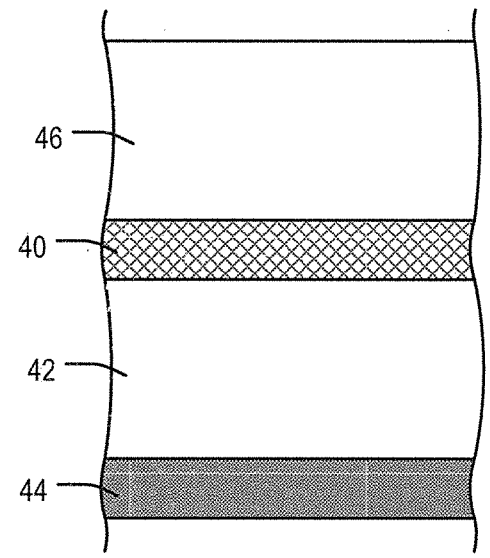
FIG. 6 is a partial sectional view of another embodiment of a composite membrane including a barrier layer positioned between two support layers.

Turning to FIG. 5, one embodiment of a composite membrane 30 includes a barrier layer 40 disposed on a support layer 42. As discussed above, the support layer 42 may be oriented toward, and in communication with, a reservoir 44. In one aspect, the support layer 42 may be configured to wick volatile material toward the barrier layer 40. In another aspect, the support layer may press inwardly as shown in FIG. 4B to maintain contact with a volatile material disposed within a reservoir. In yet another aspect, a three or more layer membrane 30' may be used as described above with the barrier layer 40 sandwiched between support layers 42 and 46. Further examples of composite membranes that may be compatible with a vapor-dispensing device according to the present disclosure are described in U.S. Pat. No. 5,032,282 to Linder et al, U.S. Pat. No. 5,039,421 to Linder et al., U.S. Pat. No. 5,024,765 to Linder et al., U.S. Pat. No. 8,597,518 to Parnas et al., U.S. Pat. No. 8,617,395 to Offerman et al. and U.S. Pat. No. 7,297,277 to Radomyselski.

Figure 7:
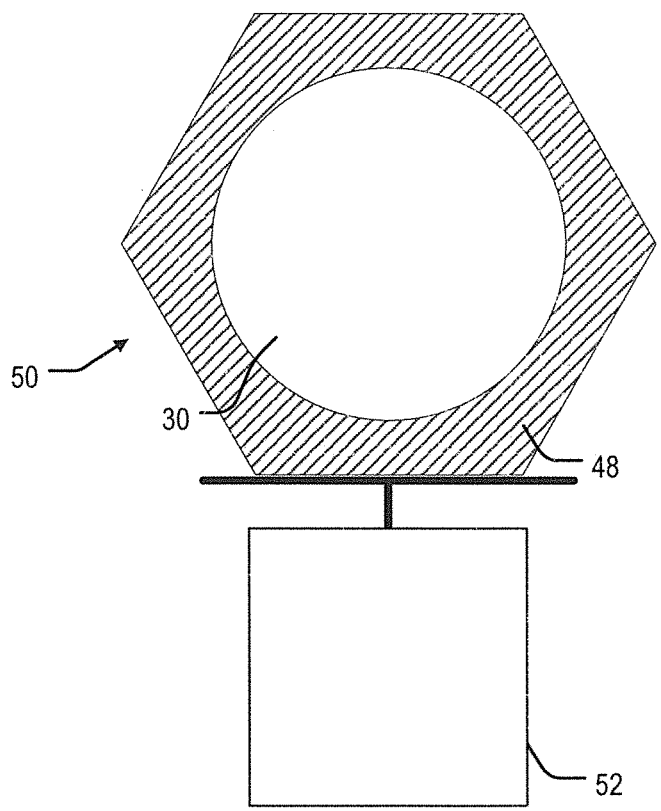
FIG. 7 is a schematic representation of a test cell including a composite membrane, a volatile composition reservoir, and a scale.

FIG. 7 shows a test cell for characterization of a composite membrane such as membrane 30. In one aspect, the membrane 30 may be in communication with a reservoir containing a volatile composition. The membrane 30 and reservoir may be supported by a frame 48 to form a test cell 50. The test cell 50 may be positioned on a mass balance or scale 52 within a test chamber.

For one experiment, the test cell 50 was fitted with a PERVATECH PDMS composite membrane (see membrane A below) with a 0.0036 m$^2$ surface area. The membrane included a barrier layer with a thickness of less than about 5 μm disposed on a support layer having a thickness of at least about 10 μm. A fragrance reservoir was filled with a volatile composition. The testing apparatus included a head-space analysis instrument. An enclosure of the instrument containing the test cell was operated at 200 liters per minute air flow. The system weight was automatically recorded every 300 seconds. Solid phase microextraction (carboxen/PDMS) was performed for sampling of emitted fragrance followed by analysis on a gas chromatograph equipped with a flame ionization detector. Sampling was performed at intervals of about 26 minutes for the first several days. Thereafter, about 10 samples were collected per day. The resulting data were used to determine the weight loss rate as a function of time.

Figure 8:
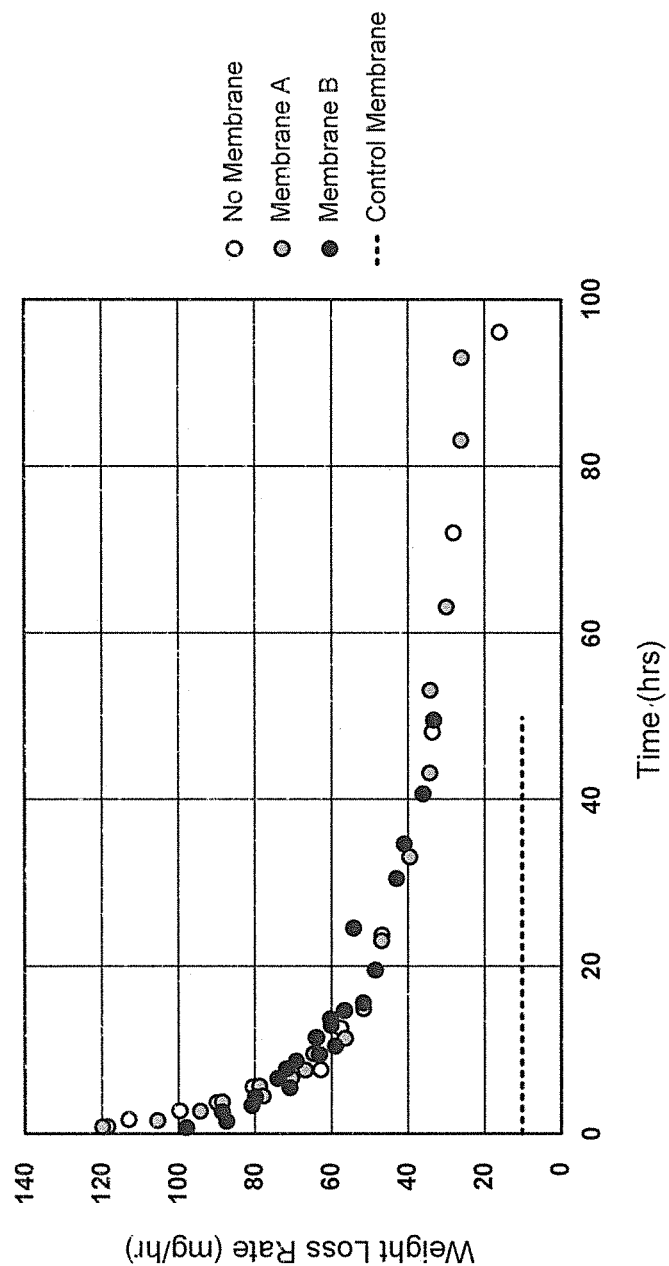
FIG. 8 is a plot of weight loss rate as a function of time with data shown for a system including no membrane, a first composite membrane A, a second composite membrane B, and a control membrane.
Figure 9:
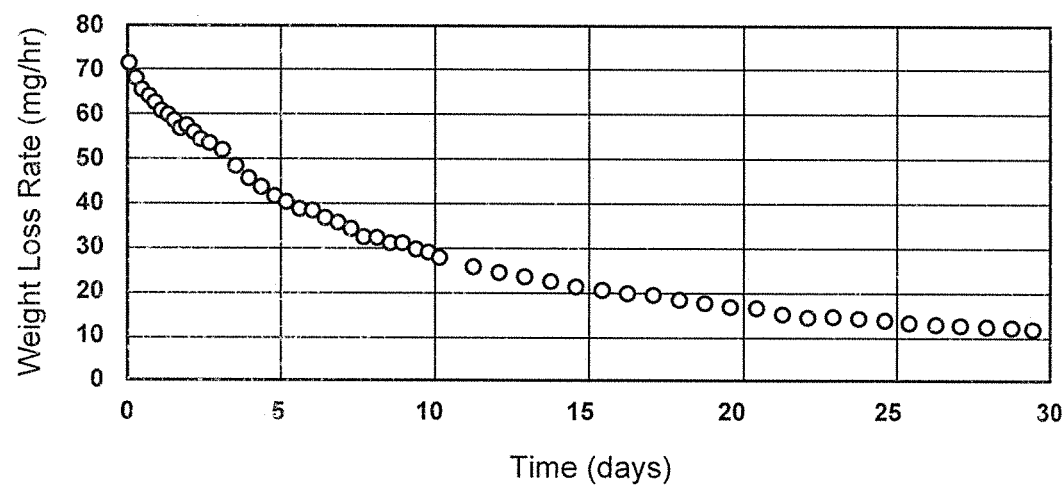
FIG. 9 is a plot of weight loss rate as a function of time with data shown for a system including a PDMS composite membrane.
Figure 11:
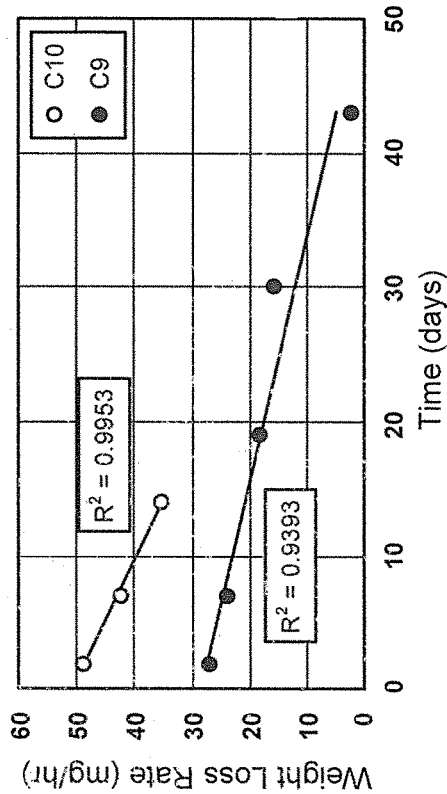
FIG. 11 is a plot of weight loss rate as a function of time for a representative PISO system with data presented for a volatile composition including a component designated C9 and a component designated C10.
Figure 13:
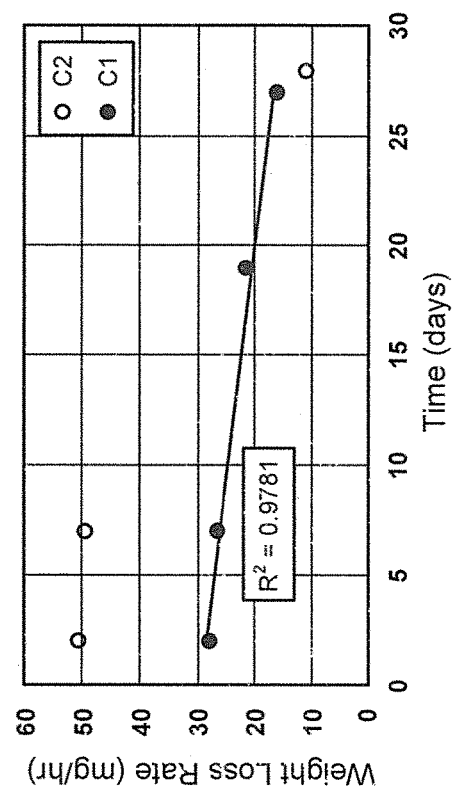
FIG. 13 is a plot of weight loss rate as a function of time for a representative PISO system with data presented for a volatile composition including a component designated C1 and a component designated C2.
Figure 10:
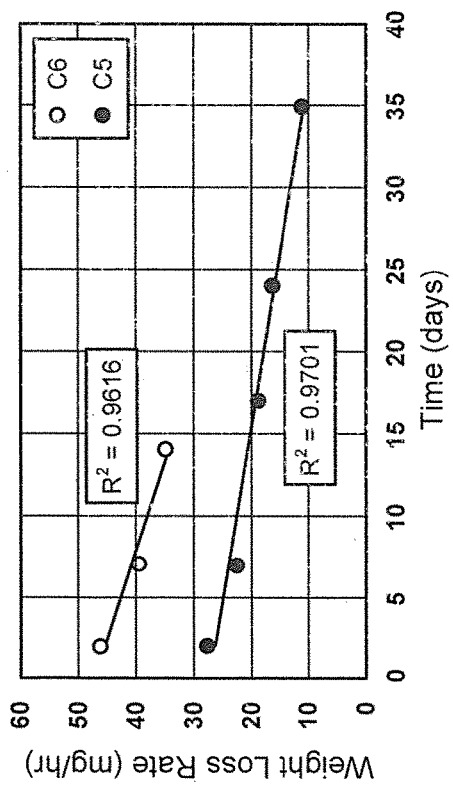
FIG. 10 is a plot of weight loss rate as a function of time for a representative PISO system with data presented for a volatile composition including a component designated C5 and a component designated C6.
Figure 12:
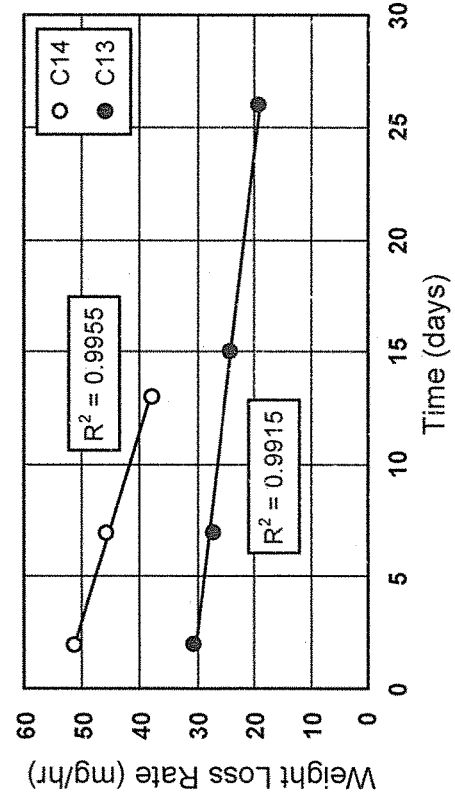
FIG. 12 is a plot of weight loss rate as a function of time for a representative PISO system with data presented for a volatile composition including a component designated C13 and a component designated C14.

Data collected with the test cell shown in FIG. 7 is illustrated in FIGS. 8 and 9. Data collected for different composite membranes A and B exhibited a weight loss rate as a function of time on par with data collected for a test cell without a membrane. Membrane A is an unsupported four thousandths PDMS membrane. Membrane B is a membrane including a PDMS layer sandwiched between two Entek high-density polyethylene layers. The absolute flux values shown in FIG. 8 are not necessarily relateable to one another, because the experiments were performed under different conditions. However, the data shown in FIG. 8 establishes that the relative rate of change of the flux is comparable for Membranes A and B when compared to no membrane. Comparing Membrane A to Membrane B, the performance characteristics are similar. However, Membrane A (PDMS without support) underwent significant bulging throughout the experiment, while Membrane B exhibited enhanced mechanical properties and did not undergo bulging.

Similar data to that shown in FIG. 8 is shown in FIG. 9 for an alternative fragrance composition and a Membrane C. Membrane C is a PERVATECH PDMS flat sheet membrane with a polyethylene terephthalate (PET) support layer having a thickness of 130 μm, a first intermediate polyisoprene layer having a thickness of about 100 μm, and a PDMS barrier layer having a thickness of between about 3 μm and about 5 μm. The PDMS layer was fully crosslinked and had a glass transition temperature of −130° C., a contact angle of 105° (±8), and a density of 1.15. In one aspect, the data in FIG. 9 illustrates the weight loss rate behavior of a composite membrane over the course of about 30 days. Peak weight loss rates were observed at about 0.07 g/hr for a 0.0036 $m^2$ membrane. In terms of maximum observed flux values, 0.07 g/hr corresponds with a flux of about 19.5 g/($m^2$-hr). Over the course of 30 days, weight loss rates were observed to drop, but remained at greater than about 0.01 g/hr. Again, it will be appreciated that the composite membrane was able to achieve elevated flux rates of up to 19.5 g/($m^2$-hr) with an average flux of about 8 g/($m^2$-hr) over the course of at least 30 days at ambient conditions. For comparison, data for a prior art PISO system having no membrane is presented in FIGS. 10-13 for proprietary fragrances. The data are designated C1, C2, C5, C6, C9, C10, C13, and C14. C1 and C2 are the same fragrance, C5 and C6 are the same fragrance, C9 and C10 are the same fragrance, and C13 and C14 are the same fragrance. C1, C5, C9, and C13 represent a low heat setting for the PISO system and C2, C6, C10, and C14 represent a high heat setting for the PISO system.

With reference to the data shown in the FIGS. 8-13, it was observed that a composite membrane operated at ambient conditions was able to transport a volatile composition with a rate of changing flux on par with a membrane-free system (i.e., a reservoir open to the atmosphere; FIG. 8) and a flux on par with a PISO system under high heat (FIGS. 10-13), which is operated at elevated temperatures. Therefore, a composite membrane according to the present disclosure may be a more versatile membrane for use in a vapor-dispensing device. In one aspect, users of a volatile dispensing device may use the device in one of several ways. For example, a user may place the device on a flat surface or attach the device to a wall, shelf, dashboard of a vehicle, or the like. The device may be activated for use such as by pressing a button, unwrapping at least a portion of the device, unfastening and opening the device, exposing a portion of the membrane, or the like. In another example, a foil layer or other obstruction layer may be removed from a surface of the membrane such as by peeling back the obstruction layer. The obstruction layer may be a barrier. However, it will be appreciated that the obstruction layer may be distinguished from the barrier layer of the composite membrane. In yet another example, the obstruction layer may be substantially impenetrable or impermeable with respect to a volatile composition disposed within a reservoir in communication with a composite membrane.

In some embodiments, a user may be able to replenish the volatile composition or material used with the vapor-dispensing device. For example, a dispenser may include a refillable reservoir, or one or more replaceable components such as a replaceable reservoir, replaceable composite membrane, replaceable dispenser housing, or combinations thereof. In one example, a refill cartridge for a dispenser may include a reservoir containing a volatile composition and a membrane coupled to the reservoir. A used cartridge (e.g., a reservoir containing a volatile composition and a membrane coupled to the reservoir) may be removed from the vapor-dispensing device. Thereafter, the refill cartridge may be placed in the location vacated by the used cartridge.

In some embodiments, a dispenser (e.g., dispenser 20) may include a heating element such as a candle, an electrical (e.g. resistive) heating element, a chemical heating element (e.g., an exothermic composition), or another like heating element. Activation of the heating element may result in a temperature of one or more components of the dispenser. As a result, a volatile may be transported at a higher rate across the composite membrane as compared with an unheated dispenser. In some embodiments, the dispenser may be plugged in to an electrical outlet in order to activate the heating element. In yet other embodiments, a composite membrane may be incorporated into an electrical heating device such as those described in U.S. Pat. Nos. 4,849,606, and 5,937,140, which are assigned to S. C. Johnson & Son, Inc., of Racine, Wis.

A composite membrane according to the present disclosure may provide a number of advantages over other types of membranes that are traditionally used for delivery of a volatile composition (e.g., non-composite or monolayer membranes) or vapor-dispensing devices incorporating those membranes. In one aspect, use of a disclosed composite membrane may enable greater overall flexibility in the design of a vapor-dispensing device. For two equal sized delivery systems, a system with a composite membrane may exhibit a greater overall flux as compared with a monolayer membrane. For example, the flux of a fragrance molecule may be about 3 to about 20 times greater for a composite membrane as compared with a monolayer membrane. Accordingly, a greater flux may be achieved for a composite membrane of the same size as a monolayer membrane.

Further, a composite membrane may enable the design of a smaller form factor vapor-dispensing device as a relatively smaller composite membrane may be able to achieve the same rate of delivery for a given volatile composition as compared with a relatively larger monolayer membrane. For example, a composite membrane having a 0.001 $m^2$ surface area may be able to achieve a rate of delivery on par with a monolayer membrane having a 0.002 m² surface area. In one example, a cyclic fragrance molecule having a molecular weight of about 240 (e.g., methyl cedryl ether) may have a flux that is about 5 times greater for a composite membrane than for a monolayer membrane of the same size. In another example, a branched fragrance molecule having a molecular weight of about 155 (e.g., linalool) may have a flux that is about 15 times greater for a composite membrane than for a monolayer membrane of the same size.

In some embodiments, a composite membrane with a higher overall flux as compared with a monolayer membrane may provide a greater range across which a volatile composition may be delivered to an environment. Accordingly, a vapor-dispensing device may be designed to enable the rate of delivery (i.e., the mass of material transported across the composite membrane per unit of time) to be adjusted or reduced relative to the maximum rate of delivery of the composite membrane. In one aspect, an adjustment to the rate of delivery may be achieved by covering a portion of the composite membrane or otherwise reducing the overall surface area of the composite membrane. Further methods for adjusting the rate of delivery may be possible including adjusting of a panel or aperture on a vapor-dispensing device incorporating a composite membrane.

In some embodiments, a composite membrane may be less selective than a monolayer membrane. A composite membrane with low selectivity may therefore transport a broader range of molecules as compared with a monolayer membrane. Accordingly, in one aspect, a composite membrane may be capable of transporting molecules having a molecular weight between about 100 and about 200. In another aspect, a composite membrane may be capable of transporting molecules having a molecular weight between about 125 and about 175. In yet another aspect, a composite membrane may be capable of transporting molecules having a molecular weight between about 140 and about 160.

In a further aspect, reduced selectivity may correlate with a broader range or pallet of molecules that may be included in a volatile composition. For example, in the case of a fragrance composition, a perfumer may be able to include a greater or more diverse range of fragrance molecules. Similarly, in the case of a pest control composition, it may be possible to work with insecticides or other pest control molecules that may not be compatible with a monolayer membrane. In some embodiments, a composite membrane or a vapor-dispensing device including a composite membrane may be configured to prevent leaks, spills, exposure or access to a volatile composition.

EXAMPLES

A number of composite membranes were selected for comparison with a monolayer membrane. For each membrane, the flux of five different fragrance molecules through the membrane was determined. The fragrance molecules had varying molecular weights (MW) and included hexyl acetate (MW=144.2), linalool (MW=154.3), linalyl acetate (MW=196.3), jasmacyclene (MW=192.3), and cedryl methyl ether (MW=236.4). Flux data for each of the fragrance molecules is provided in Tables 1-5. Selected membranes were manufactured by either PERVATEVCH or POLYMER PLUS as indicated.

TABLE 1

| | Hexyl Acetate Flux $[g \cdot hr^{-1} \cdot m^2]$ | | |
|---|---|---|---|
| Membrane Type | Day 1 | Day 2 | Day 3 |
| ABX Membrane | 0.309 | 0.324 | 0.326 |
| PDMS Composite Membrane[1] | 3.401 | 2.395 | 1.523 |
| POMS Composite Membrane[2] | 3.812 | 2.417 | 1.462 |
| polyether block amide composite membrane 1[3] | 3.287 | 2.519 | 1.494 |
| polyether block amide composite membrane 2[3] | 3.370 | 2.329 | 1.475 |
| 4 mil GLS LC 436-159[3] | 2.748 | 2.219 | 1.600 |

[1]PERVATECH (see Membrane C)
[2]PERVATECH (polyoctylmethylsiloxane (POMS) substituted for PDMS in Membrane C)
[3]POLYMER PLUS

TABLE 2

| | Linalool Flux $[g \cdot hr^{-1} \cdot m^2]$ | | |
|---|---|---|---|
| Membrane Type | Day 1 | Day 2 | Day 3 |
| ABX Membrane | 0.020 | 0.023 | 0.023 |
| PDMS Composite Membrane[1] | 0.322 | 0.303 | 0.260 |
| POMS Composite Membrane[2] | 0.326 | 0.288 | 0.244 |
| polyether block amide composite membrane 1[3] | 0.325 | 0.325 | 0.259 |
| polyether block amide composite membrane 2[3] | 0.337 | 0.302 | 0.248 |
| 4 mil GLS LC 436-159[3] | 0.254 | 0.247 | 0.238 |

[1]PERVATECH (see Membrane C above)
[2]PERVATECH (POMS substituted for PDMS in Membrane C)
[3]POLYMER PLUS

TABLE 3

| | Linalyl Acetate Flux $[g \cdot hr^{-1} \cdot m^2]$ | | |
|---|---|---|---|
| Membrane Type | Day 1 | Day 2 | Day 3 |
| ABX Membrane | 0.072 | 0.079 | 0.082 |
| PDMS Composite Membrane[1] | 0.879 | 0.853 | 0.703 |
| POMS Composite Membrane[2] | 0.848 | 0.802 | 0.688 |
| polyether block amide composite membrane 1[3] | 0.810 | 0.838 | 0.802 |
| polyether block amide composite membrane 2[3] | 0.921 | 0.889 | 0.781 |
| 4 mil GLS LC 436-159[3] | 0.693 | 0.697 | 0.653 |

[1]PERVATECH (see Membrane C above)
[2]PERVATECH (POMS substituted for PDMS in Membrane C)
[3]POLYMER PLUS

TABLE 4

| | Jasmacyclene Flux $[g \cdot hr^{-1} \cdot m^2]$ | | |
|---|---|---|---|
| Membrane Type | Day 1 | Day 2 | Day 3 |
| ABX Membrane | 0.034 | 0.035 | 0.036 |
| PDMS Composite Membrane[1] | 0.091 | 0.096 | 0.126 |
| POMS Composite Membrane[2] | 0.087 | 0.119 | 0.128 |
| polyether block amide composite membrane 1[3] | 0.089 | 0.098 | 0.149 |
| polyether block amide composite membrane 2[3] | 0.095 | 0.117 | 0.151 |
| 4 mil GLS LC 436-159[3] | 0.080 | 0.083 | 0.082 |

[1]PERVATECH (see Membrane C above)
[2]PERVATECH (POMS substituted for PDMS in Membrane C)
[3]POLYMER PLUS

TABLE 5

| Membrane Type | Cedryl Methyl Ether Flux [g · hr$^{-1}$ · m$^2$] | | |
|---|---|---|---|
| | Day 1 | Day 2 | Day 3 |
| ABX Membrane | 0.003 | 0.004 | 0.004 |
| PDMS Composite Membrane[1] | 0.007 | 0.008 | 0.019 |
| POMS Composite Membrane[2] | 0.006 | 0.015 | 0.020 |
| polyether block amide composite membrane 1[3] | 0.007 | 0.008 | 0.020 |
| polyether block amide composite membrane 2[3] | 0.007 | 0.010 | 0.022 |
| 4 mil GLS LC 436-159[3] | 0.006 | 0.006 | 0.007 |

[1]PERVATECH (see Membrane C above)
[2]PERVATECH (POMS substituted for PDMS in Membrane C)
[3]POLYMER PLUS Based on the flux values provided in Tables 1-5, an enhancement factor can be calculated for each of the composite membranes with respect to the monolayer membrane. In one aspect, the enhancement factor may be defined as the flux value for a given species for a given composite membrane divided by the flux value for the same species for a reference monolayer membrane. Accordingly, the enhancement factor for hexyl acetate on Day 1 for the PDMS composite membrane is 3.401/0.309=11.0 (see Table 1). The enhancement factor may be indicative of the extent to which the flux of a given molecule through a composite membrane is improved (i.e., increased) over a reference monolayer membrane under comparable conditions.

In some embodiments, an enhancement factor for a given composite membrane relative to a monolayer membrane may be between about 1.5 and about 20. In one example, an enhancement factor for a composite membrane may be at least about 3. In another example, an enhancement factor for a composite membrane may be at least about 5. In yet another example, an enhancement factor for a composite membrane may be at least about 10. In a further example, an enhancement factor for a composite membrane may be at least about 12. In still another example, an enhancement factor for a composite membrane may be at least about 15.

In another aspect, based on the flux values provided in Tables 1-5, a selectivity factor may be calculated for each of the composite membranes. In one aspect, the selectivity factor may be defined as the flux value for a first species for a given membrane divided by the flux value for a second species for the same membrane. Accordingly, the selectivity factor for hexyl acetate relative to linalool for the PDMS composite membrane on Day 1 may be calculated as 3.401/0.322=10.6 (see Tables 1 and 2). By comparison, the selectivity factor for hexyl acetate relative to linalool for the monolayer membrane on Day 1 may be calculated as 0.309/0.020=15.1 (see Tables 1 and 2). The selectivity factor may be indicative of the extent to which the flux of a two different molecules through a composite membrane is similar under comparable conditions. In one aspect, a selectivity factor approaching unity (i.e., selectivity factor≈1) may be indicative that the flux behavior for two different molecules for a given membrane is similar. Further, a selectivity factor approaching unity may be indicative that a membrane is generally non-selective or has a low selectivity for two distinct molecules.

In another aspect, the selectivity factors for two different membranes can be compared to determine a selectivity enhancement factor. In one aspect, the selectivity enhancement factor may be defined as the ratio of a first selectivity factor for a first membrane and a second selectivity factor for a second membrane where each of the first and second selectivity factors are calculated with respect to the same two distinct molecules. Accordingly, the selectivity enhancement factor for hexyl acetate relative to linalool for the PDMS composite membrane relative to the monolayer membrane on Day 1 may be calculated as 10.6/15.1=0.7 (see Tables 1 and 2 and discussion of selectivity factors).

The selectivity enhancement factor may be indicative of the extent to which the selectivity of a first membrane for two different molecules is comparable to a second membrane under similar testing conditions. In one aspect, a selectivity enhancement factor approaching unity (i.e., selectivity enhancement factor≈1) may be indicative that the selectivity of two different membranes is similar. However, a selectivity enhancement factor <1 may be indicative that the first membrane is less selective than the second membrane with respect to two distinct species. Therefore, it may be useful to provide a (first) composite membrane with a selectivity enhancement factor <1 relative to a (second) monolayer membrane.

It will be appreciated that a selectivity factor or selectivity enhancement factor may not be equivalent to a selectivity or ratio of selectivities. Notably, the selectivity, as defined in Eq. 6 is equal to the ratio of the permeabilities of two different molecules for a given membrane. While permeability is proportional to flux, the permeability is further dependent on the position of the molecule (species) in the membrane and the transmembrane concentration as described in Eq. 5 above. However, the selectivity enhancement factor may still provide an estimate or indication of the relative selectivity of a membrane.

In some embodiments, a composite membrane or a layer thereof may be characterized by a strength factor. The strength factor may be based on a characteristic of a layer of the composite membrane such as a bending moment, a modulus of elasticity, a thickness, a surface area, or another dimension or material property. In another aspect, a strength ratio may be used to compare two layers of a membrane. For example, the strength ratio may be defined as the ratio of the strength factors for two layers of a composite membrane. In some embodiments, it may be useful to specify a minimum strength ratio for a composite membrane.

Those skilled in the art will appreciate the numerous variations that may be made with respect to the present disclosure and which are intended to be captured herein. Other embodiments include all of the various combinations of individual features of each of the embodiments described herein.

All documents cited in the Detailed Description of the Invention are, in relevant part, incorporated herein by reference; the citation of any document is not to be construed as an admission that it is prior art with respect to the present invention.

INDUSTRIAL APPLICABILITY

Embodiments of a composite membrane and vapor-dispensing system described herein advantageously combine the features of a low selectivity barrier layer for transport of a broad range of molecules at relatively high fluxes with a support layer that provides mechanical strength without limiting the rate of transport across the composite membrane. Accordingly, the disclosed composite membrane and vapor-dispensing system may be used across a broad range of applications.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

What is claimed is:

1. A refill cartridge for a volatile composition, comprising:
   a reservoir;
   a volatile composition within the reservoir;
   a blister defining a cup-shaped structure having a top edge;
   a composite membrane in fluid communication with the reservoir, the composite membrane including a barrier layer having a thickness of less than 10 µm and at least one support layer in contact with the barrier layer, the support layer having a thickness of at least 10 µm, the support layer being between the barrier layer and the reservoir, the support layer being a wicking layer configured to enhance transport of the volatile composition toward the barrier layer; and
   a peripheral flange coupled to and extending outwardly from the top edge of the cup-shaped structure, the composite membrane being coupled to at least one of the blister and the peripheral flange, thereby defining the reservoir,
   wherein the volatile composition is transported from the reservoir across the composite membrane at a flux of between at least 30 and 100 g/(m$^2$·hr) at 25° C. and 101 kPa, and an average flux of about 8 g/(m$^2$-hr) over the course of at least 30 days, and
   wherein the composite membrane is capable of transporting molecules having a molecular weight of between substantially 140 and substantially 160.

2. The refill cartridge of claim 1, wherein the volatile composition is a fragrance, a sanitizer, an air freshener, a fabric freshener, a cleaner, an odor eliminator, a mold inhibitor, a mildew inhibitor, an insect repellent, an insecticide, an aromatherapeutic molecule, or a molecule selected from the group consisting of $C_1$-$C_{20}$ aldehydes, $C_3$-$C_{20}$ ketones, and $C_1$-$C_{20}$ alcohols.

3. The refill cartridge of claim 1, wherein the cup-shaped structure further includes a rectangular bottom wall and four side walls, the top edge extending around a periphery of the four side walls, and wherein the composite membrane is coupled to at least one of the blister and the peripheral flange by heat sealing.

4. The refill cartridge of claim 1, wherein a flux of cedryl methyl ether through the membrane is at least 0.006 g/(m$^2$·hr) at 25° C. and 101 kPa.

5. The refill cartridge of claim 1, wherein a selectivity of the composite membrane for a first molecule of the volatile composition relative to a second molecule of the volatile composition is less than 1000, and wherein the second molecule is different from the first molecule.

6. The refill cartridge of claim 1, wherein an enhancement factor for the composite membrane relative to a monolayer membrane is at least 3.

7. The refill cartridge of claim 1, wherein a selectivity enhancement factor for the composite membrane relative to a monolayer membrane is less than 1.

8. A refill cartridge for a volatile composition, comprising:
   a reservoir;
   a volatile composition within the reservoir;
   a blister defining a cup-shaped structure having a top edge;
   a composite membrane in fluid communication with the reservoir, the composite membrane including a first support layer having a thickness of at least 10 µm, a second support layer having a thickness of at least 10 µm, and a barrier layer intermediate the first support layer and the second support layer, the barrier layer having a thickness of less than 10 µm, the first support layer being between the barrier layer and the reservoir, the first support layer being a wicking layer configured to enhance transport of the volatile composition toward the barrier layer; and
   a peripheral flange coupled to and extending outwardly from the top edge of the cup-shaped structure, the composite membrane being coupled to at least one of the blister and the peripheral flange, thereby defining the reservoir,
   wherein the volatile composition is transported from the reservoir across the composite membrane at a flux of between at least 30 and 100 g/(m$^2$·hr) at 25° C. and 101 kPa, and an average flux of about 8 g/(m$^2$-hr) over the course of at least 30 days,
   wherein the volatile composition comprises a plurality of fragrance molecules,
   wherein the fragrance molecules are transported from the reservoir across the composite membrane at a flux of at least 0.006 g/(m$^2$·hr) at 25° C. and 101 kPa, and
   wherein the composite membrane is capable of transporting molecules having a molecular weight of between substantially 140 and substantially 160.

9. The refill cartridge of claim 8, wherein the volatile composition is a fragrance, a sanitizer, an air freshener, a fabric freshener, a cleaner, an odor eliminator, a mold inhibitor, a mildew inhibitor, an insect repellent, an insecticide, an aromatherapeutic molecule, or a molecule selected from the group consisting of $C_1$-$C_{20}$ aldehydes, $C_3$-$C_{20}$ ketones, and $C_1$-$C_{20}$ alcohols.

10. The refill cartridge of claim 8, wherein a flux of hexyl acetate through the membrane is at least 1.462 g/(m$^2$·hr) at 25° C. and 101 kPa.

11. A vapor-dispensing device, comprising:
   a housing;
   a composite membrane disposed in the housing, the composite membrane having a barrier layer with a thickness of less than 10 µm and at least one support layer in contact with the barrier layer, the support layer having a thickness of at least 10 µm;
   a reservoir disposed in the housing and in fluid communication with the composite membrane;
   a volatile composition within the reservoir;
   a blister defining a cup-shaped structure having a top edge; and
   a peripheral flange coupled to and extending outwardly from the top edge of the cup-shaped structure, the composite membrane being coupled to at least one of the blister and the peripheral flange, thereby defining the reservoir,
   wherein the volatile composition is transported from the reservoir across the composite membrane at a flux of between at least 30 and 100 g/(m$^2$-hr) at 25° C. and 101 kPa, and an average flux of about 8 g/(m$^2$-hr) over the course of at least 30 days,
   wherein the support layer is between the barrier layer and the reservoir,
   wherein the composite membrane is capable of transporting molecules having a molecular weight of between substantially 140 and substantially 160,
   wherein the support layer is a wicking layer configured to enhance transport of the volatile composition toward the barrier layer, and wherein the barrier layer is characterized by a low selectivity for transport of the volatile composition.

12. The device of claim 11, further comprising a fan within the housing.

13. The device of claim 11, further comprising a heating element within the housing.

14. The device of claim 11, further comprising an adjustable cover disposed over at least a portion of a surface of the composite membrane, wherein the cover is operable to vary a fraction of the surface that is in communication with an exterior of the housing.

* * * * *